(12) United States Patent
Auriol et al.

(10) Patent No.: US 9,107,852 B2
(45) Date of Patent: Aug. 18, 2015

(54) USES OF AGONISTS OF DELTA OPIOID RECEPTOR IN COSMETIC AND DERMOCOSMETIC FIELD

(71) Applicant: Induchem Holding AG, Volketswil (CH)

(72) Inventors: Daniel Auriol, Toulouse (FR); Fabrice Lefevre, Auterive (FR); Kuno Schweikert, Pfäffikon SZ (CH); Gérard Redziniak, Antony (FR)

(73) Assignee: INDUCHEM HOLDING AG, Volketswil (CH)

( * ) Notice: Subject to any disclaimer, the term of this patent is extended or adjusted under 35 U.S.C. 154(b) by 0 days.

(21) Appl. No.: 13/848,937

(22) Filed: Mar. 22, 2013

(65) Prior Publication Data

US 2013/0251657 A1     Sep. 26, 2013

(30) Foreign Application Priority Data

Mar. 23, 2012  (EP) ..................................... 12305335

(51) Int. Cl.
| | |
|---|---|
| A61K 8/60 | (2006.01) |
| A61K 8/64 | (2006.01) |
| A61Q 1/02 | (2006.01) |
| A61Q 19/08 | (2006.01) |
| A61Q 5/00 | (2006.01) |
| A61Q 19/00 | (2006.01) |
| A61Q 5/02 | (2006.01) |
| A61Q 5/10 | (2006.01) |
| A61Q 17/04 | (2006.01) |

(52) U.S. Cl.
CPC . *A61K 8/64* (2013.01); *A61K 8/645* (2013.01); *A61Q 5/00* (2013.01); *A61Q 19/00* (2013.01); *A61Q 19/08* (2013.01); *A61Q 5/02* (2013.01); *A61Q 5/10* (2013.01); *A61Q 17/04* (2013.01)
USPC .......................................................... 514/1.1

(58) Field of Classification Search
None
See application file for complete search history.

(56) References Cited

FOREIGN PATENT DOCUMENTS

| | | |
|---|---|---|
| EP | 1595541 | 11/2005 |
| WO | WO 2009/012376 | 1/2009 |
| WO | WO 2009012376 A1 * | 1/2009 |

OTHER PUBLICATIONS

Yang et al., "Structure-activity relationship of rubiscolins as δ opioid peptides", Peptides 24:503-508 (2003)—copy provided in Applicant's IDS dated Mar. 22, 2013.*
UniprotKB/Swiss-Prot Accession No. P05422, accessed Jun. 14, 2014 at URL: uniprot.org/uniprot/P05422.*
UniprotKB/Swiss-Prot Accession No. I6TF82 (accessed Jun. 14, 2014 at URL: uniprot.org/uniprot/ I6TF82).*
Yang et al. (Peptides 24:503-508 (2003).*
Hirata, H. et al. "Rubiscolin-6, a δ opioid peptide derived from spinach Rubisco, has anxiolytic effect via activating $\delta_1$ and dopamine $D_1$ receptors" *Peptides*, 2007, pp. 1998-2003, vol. 28.
Yang, S. et al. "Structure—activity relationship of rubiscolins as δ opioid peptides" *Peptides*, 2003, pp. 503-508, vol. 24.
European Search Report in priority Application No. 12305335.7, Nov. 5, 2012, pp. 1-10.

* cited by examiner

*Primary Examiner* — Julie Ha
*Assistant Examiner* — Kristina M Hellman
(74) *Attorney, Agent, or Firm* — Saliwanchik, Lloyd & Eisenschenk

(57) ABSTRACT

The present invention relates to the use of a DOR ligand for stimulating pigmentation in a cosmetic composition and to the use of rubiscolin-6 or its derivatives in a cosmetic composition.

16 Claims, 4 Drawing Sheets

FIGURE 1A
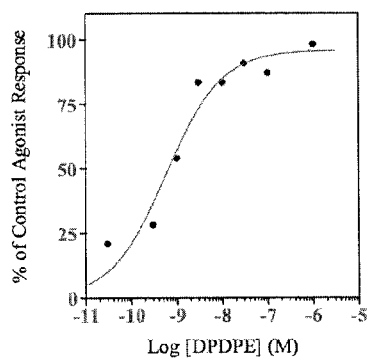
FIGURE 1B
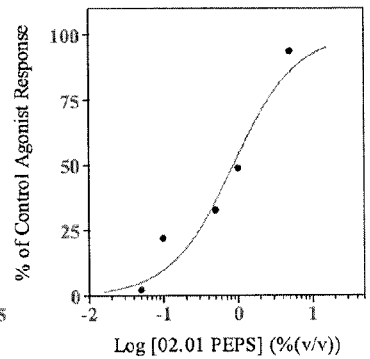
FIGURE 1C
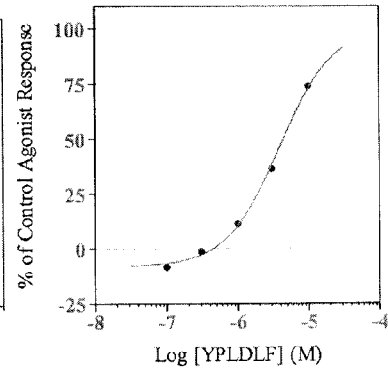
FIGURE 2
FIG 2A
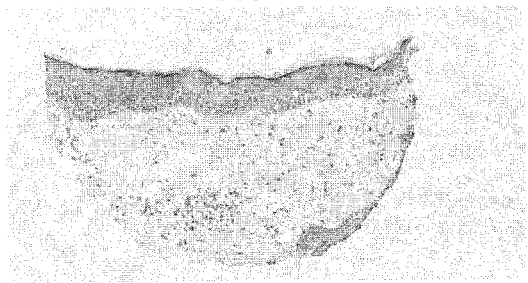
FIG 2B
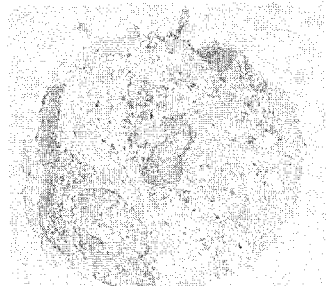
FIG 2C
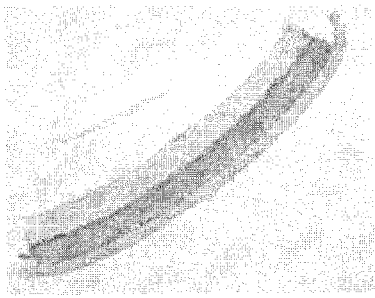
FIG 2D
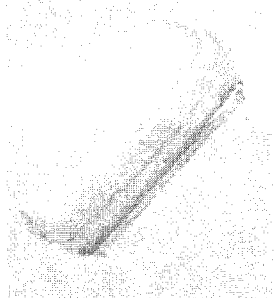
FIG 2E

USES OF AGONISTS OF DELTA OPIOID RECEPTOR IN COSMETIC AND DERMOCOSMETIC FIELD

The Sequence Listing for this application is labeled "Seq-List.txt" which was created on Mar. 20, 2013 and is 8 KB. The entire contents of the sequence listing is incorporated herein by reference in its entirety.

FIELD OF THE INVENTION

The present invention relates to the cosmetic and dermocosmetic field.

PRIOR ART

Opioids receptors are part of the super family of G-protein coupled receptors (GPCR) which have seven trans-membrane domains. Upon activation by their respective ligands outside the cell, GPCR release G-protein under an activated form in the cytoplasm, which in turns activates several target proteins in the cell such as adenylate cyclase.

The most well-known opioid receptors are the mu receptors (MOR), for which morphine is the ligand. Two other families of opioid receptors have been described in addition to the mu receptors: the delta and the kappa receptors.

Opioid receptors are known to be involved in the control of the sensation of pain.

However, recent studies have shown that deletion of mu and kappa opioid receptors in mice changes epidermal hypertrophy, density of peripheral nerve endings, and itch behavior (Bigliardi et al. 2007). These receptors were therefore considered not only to be linked to pain and itch sensation, but also to the control of skin differentiation.

In the same approach, scientific studies have demonstrated that the deletion of DOR (delta opioid receptors) in mice leads to the formation of an abnormal thin epidermis. These results suggested an essential role of DOR in skin differentiation, proliferation, and migration, factors that are important for wound healing (Bigliardi et al. 2006).

Skin and brain share the same embryologic origin during the development of the human embryo. Scientists demonstrated that opioid receptors were found to be present on the surface of both neurons and skin cells (Bigliardi et al., 2009), showing that opioids receptors are not uniquely localized in the nervous system but also in other organs such as skin. This discovery opened the door to explain why deletion of opioid receptors could interact with the proper development of skin.

Many chemical compounds are known to interact with opioid receptors: exogeneous compounds like opioids, or endogenous ones such as enkephalins and endorphins. Some peptides derived from food have also been described to act on opioid receptors. For example, small peptides originating from the digestion of the RubisCo protein, in particular rubiscolin-5 and rubiscolin-6 were shown to be ligands of DOR, but not of MOR (Yang et al., 2001; Yang et al, 2003). As these peptides are the result of digestive enzymes, it was considered that they could be involved in a neuro calming action after digestion in our gut. In addition, the rubiscolin-6, when orally administered, has been shown to enhance memory consolidation. However, due to their digestive origins, nobody imagined to use such peptides for any kind of topical applications.

If opioid receptors look like interesting targets to regulate skin's differentiation, so far nobody has ever tried to act on these receptors with agonists or antagonists to control the evolution of skin or hairs, such as reversing signs of aging or modulating pigmentation. The main reasons for this fact are the followings:

Opioid receptors are considered by scientists as pharmacological targets only dedicated to the control of pain (for example for the screening and design of new pain relief molecules). Therefore, people from the skin care industry would avoid acting on such category of cellular targets, being afraid that this could have reverse side effects.

Acting on these receptors at the skin level would only be considered as a way to control itching, painful sensations and neuro-inflammation in therapeutic indications.

There are no obvious link between delta opioid receptors and the pigmentation process of skin or hairs: using delta opioids or opioid related drugs has never been recognized as a way of modifying skin or hair color.

There are no obvious link between opioid receptors and the normalization of skin metabolism: if deletion of opioid receptor leads to abnormal skins in mice, nobody has ever demonstrated that acting on opioid receptors could reverse this phenotype. All the more, there is no evidence that the use of opioids such as morphine could reverse signs of aging and erase wrinkles on the human skin.

There is only one document, WO 2009/012376, suggesting the use of delta opioid receptor agonist in a cosmetic composition, in particular as anti-aging component for the skin. The experimental section consists in an assay with deltorphin, an endogenous component which crosses the brain-blood barrier (BBB). Accordingly, due to the endogenous nature of deltorphin and its ability to cross the BBB, the use of agonist might be associated with reverse side effects.

SUMMARY OF THE INVENTION

In a first aspect of the invention, the inventors surprisingly discovered that agonists of delta opioid receptor (DOR agonists) activate the pigmentation. Therefore the present invention relates to the use of a DOR ligand, preferably DOR agonist, for stimulating pigmentation of skin or hair, in particular for preparing a cosmetic composition for topical, intradermic, transdermic or subcutaneous administration, preferably for topical administration, for stimulating pigmentation of skin or hair. The present invention also relates to a hair care product such as shampoo or a hair-conditioning comprising a DOR ligand, preferably a DOR agonist. It further relates to a DOR ligand, preferably a DOR agonist for use in stimulating pigmentation of skin or hair. Preferably, the DOR agonist is selective for DOR. Preferably, the DOR agonist is selected from the group consisting of BU-48, SNC-80, C-8813, DPI-287, DPI-221, TAN-67, BW373U86, SIOM, RWJ-394,674, rubiscolin-6 and its derivatives having an activity of agonist of δ opioid receptor, deltorphin and its derivatives having an activity of agonist of δ opioid receptor, DPDPE, DSLET, JOM-13, DSTBULET, BUBU, and BUBUC. More preferably, the DOR agonist is a peptide selected from rubiscolin-6 and its derivatives having an activity of agonist of δ opioid receptor. Still more preferably, the agonist of δ opioid receptor is a peptide which has or comprises the sequence of formula (I)

(I)

Y-P-X1-D-X2-X3

(SEQ ID No 6)

wherein X1 being a non-aromatic hydrophobic amino acid, preferably selected from the group consisting of L, I, M, V and A, more preferably selected from the group consisting of L, I, and M;

X2 being a non-aromatic hydrophobic amino acid, preferably selected from the group consisting of L, I, and M, more preferably selected from the group consisting of L and I; and X3, present or absent, being a hydrophobic amino acid, preferably selected from the group consisting of F, L, I, M, V and A, more preferably selected from the group consisting of F, I, and V, and in particular being F or V.

In particular, the agonist of δ opioid receptor is a peptide selected from the group consisting of or a peptide having an activity of agonist of δ opioid receptor and comprising a sequence selected in the group consisting of YPLDLF (SEQ ID No 1), YPIDLF (SEQ ID No 7), YPMDLF (SEQ ID No 8), YPLDIF (SEQ ID No 9), YPLDLL (SEQ ID No 10), YPLDLI (SEQ ID No 11), YPLDLM (SEQ ID No 12), YPLDLV (SEQ ID No 13), YPLDLA (SEQ ID No 14), YPIDLV (SEQ ID No 15), YPMDLV (SEQ ID No 16), YPLDIV (SEQ ID No 17), YPIDIV (SEQ ID No 18), YPMDIV (SEQ ID No 19), YPIDLV (SEQ ID No 20), YPIDMV (SEQ ID No 21), YPIDII (SEQ ID No 22), YPMDII (SEQ ID No 23), YPMDL (SEQ ID No 24), YPIDL (SEQ ID No 25), and YPMDI (SEQ ID No 26). Even more preferably, the peptide is YPLDLF (SEQ ID No 1).

In a second aspect, the invention relates to a cosmetic composition for topical, intradermic, transdermic or subcutaneous administration, preferably for topical administration, comprising a peptide selected from rubiscolin-6 and its derivatives and at least one cosmetic additive. It also relates to the use of rubiscolin-6 and its derivatives for the preparation of a cosmetic composition for topical, intradermic, transdermic or subcutaneous administration, preferably for topical administration. It further relates to a peptide selected from rubiscolin-6 and its derivatives for use in the preparation of a cosmetic composition for topical, intradermic, transdermic or subcutaneous administration, preferably for topical administration. It relates to a peptide selected from rubiscolin-6 and its derivatives for use as cosmetic agent. Preferably, the cosmetic composition is for preventing and/or reversing the sign of skin aging, and/or refilling wrinkles, improving skin smoothness, and/or equalizing unbalanced markers in stressed skin, and/or normalizing disturbed gene expression in skin cells, and/or erasing crow's feet wrinkles, and/or recovering skin moisturization, and/or preventing trans-epidermal water loss in skin, and/or reactivating skin cells differentiation, and/or stimulating pigmentation of skin or hair.

Preferably, the peptide is a peptide which has or comprises the sequence of formula (I)

(I)
(SEQ ID No 6)
Y-P-X1-D-X2-X3 wherein X1 being a non-aromatic hydrophobic amino acid, preferably selected from the group consisting of L, I, M, V and A, more preferably selected from the group consisting of L, I, and M;

X2 being a non-aromatic hydrophobic amino acid, preferably selected from the group consisting of L, I, and M, more preferably selected from the group consisting of L and I; and X3, present or absent, being a hydrophobic amino acid, preferably selected from the group consisting of F, L, I, M, V and A, more preferably selected from the group consisting of F, I, and V, and in particular being F or V.

More preferably, the peptide is a peptide selected from the group consisting of or a peptide having an activity of agonist of δ opioid receptor and comprising a sequence selected in the group consisting of YPLDLF (SEQ ID No 1), YPIDLF (SEQ ID No 7), YPMDLF (SEQ ID No 8), YPLDIF (SEQ ID No 9), YPLDLL (SEQ ID No 10), YPLDLI (SEQ ID No 11), YPLDLM (SEQ ID No 12), YPLDLV (SEQ ID No 13), YPLDLA (SEQ ID No 14), YPIDLV (SEQ ID No 15), YPMDLV (SEQ ID No 16), YPLDIV (SEQ ID No 17), YPIDIV (SEQ ID No 18), YPMDIV (SEQ ID No 19), YPIDLV (SEQ ID No 20), YPIDMV (SEQ ID No 21), YPIDII (SEQ ID No 22), YPMDII (SEQ ID No 23), YPMDL (SEQ ID No 24), YPIDL (SEQ ID No 25), and YPMDI (SEQ ID No 26). Even more preferably, the peptide is YPLDLF (SEQ ID No 1).

In an addition aspect, the present invention relates to a device comprising a peptide selected from rubiscolin-6 and its derivatives, the device being capable of delivering said peptide via intraepidermal and/or intradermal and/or subcutaneous injection.

BRIEF DESCRIPTION OF THE DRAWINGS

FIGS. 1A-1C: Agonist effect of compound at the Delta2 receptor (DOP). FIG. 1A with DPDPE, EC50=5.9 $10^{-10}$ M, A=0.0, D=95.8. FIG. 1B with fractions of proteins hydrolyzed with pepsin 02.01 PEPS, EC50=0.87% (v/v), A=0.0, D=100.0. FIG. 1C with YPLDLF, EC50=3.9 $10^{-6}$ M, A=−8.3, D=100.0.

FIGS. 2A-2E: Effect of cytokines on the expression level of DOR in epidermis. FIG. 2A: Normal human skin—epidermis and dermis; FIG. 2B: Normal human skin—dermis and sebaceous glands; FIG. 2C: Reconstructed human epidermis (RHE); FIG. 2D: RHE treated with PMA at 2 μg; FIG. 2E: RHE treated with mix of cytokines (IL-17+OSM+TNF-α).

FIG. 3A: Melanin formation in human skin explants UVA-irradiated or treated with the peptide for 6 days. Melanin: dark brown spots on the pictures. FIG. 3B: Melanin quantification in basal layer keratinocytes from human skin explants UVA-irradiated or treated with the peptide solutions for 6 days (*p<0.01 vs Untreated Control, Student's t Test). FIG. 3C: Melanosomes quantification in melanocytes from human skin explants UVA irradiated or treated with the peptide solutions for 6 days.

FIG. 4A: mean of the percentage variations vs T0 obtained for the trans epidermal water loss parameter; FIG. 4B: mean of the percentage variations vs T0 obtained for the skin moisturizing parameter; FIG. 4C: mean of the percentage variations vs T0 obtained for the wrinkle depth parameter; FIG. 4D: mean of the percentage variations vs T0 obtained for the Rz parameter (skin wrinkledness). Dark grey bar is PHN and white outlined bar is PHG.

DETAILED DESCRIPTION OF THE INVENTION

Figure 3A:
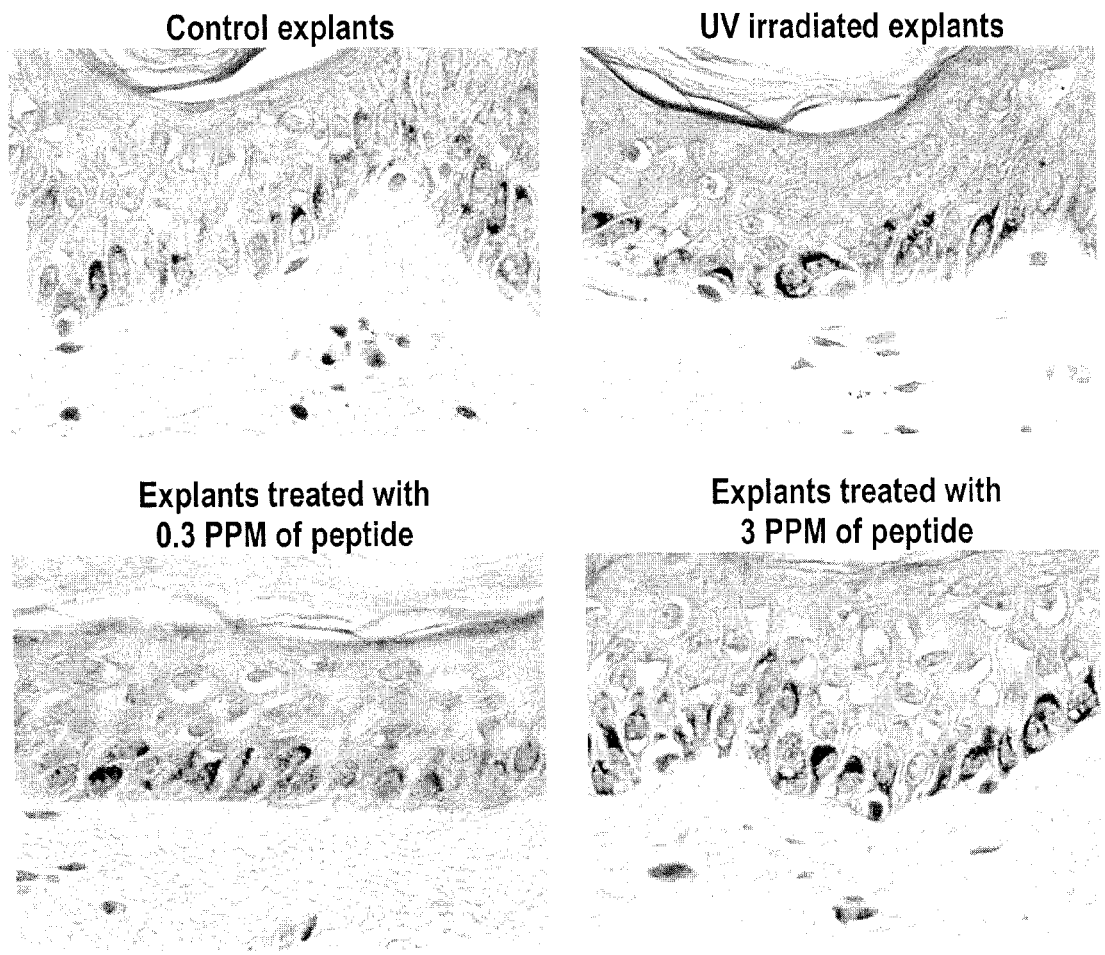
FIGS. 3A-3C.
Figure 3C:
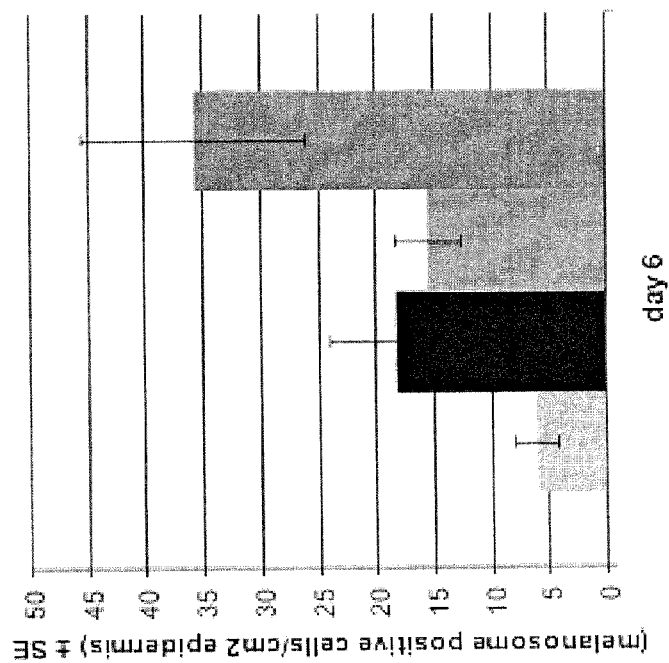
Figure 3B:
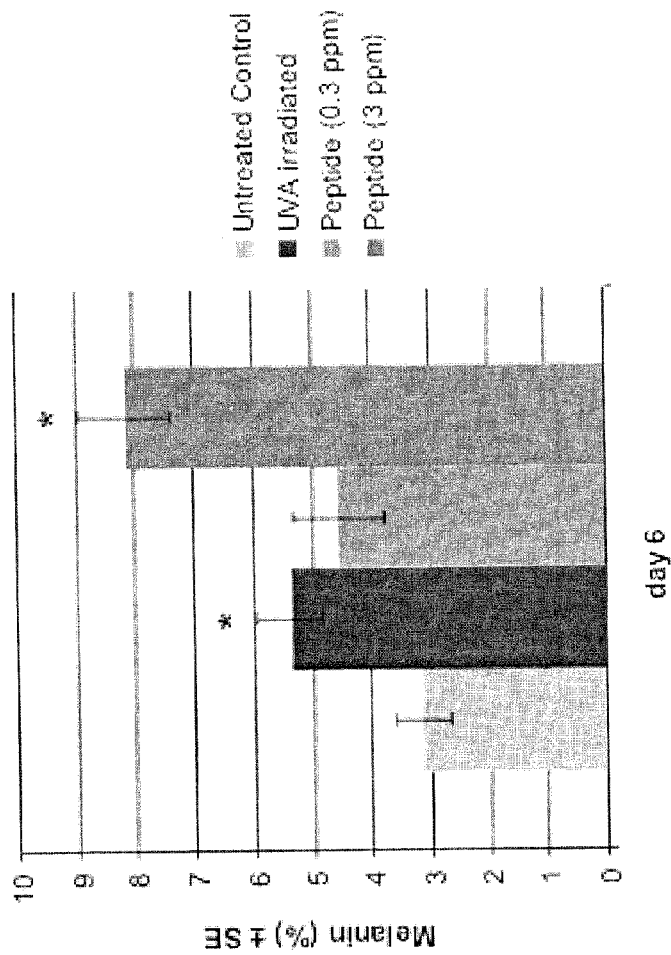

The inventors surprisingly discovered that one can act on delta opioid receptor and reverse aging process and have positive effects on skin or hairs, such as reversing the signs of aging, recovering skin's smoothness, activating melanin production, refilling deep wrinkles, increasing skin's natural moisturization. Even more surprisingly, they discovered that peptides produced by digestion of plant proteins have this capability to regulate skin differentiation processes. In addition, they surprisingly discovered that one can act on delta opioid receptor and stimulate the skin and hair pigmentation.

1. Peptides and Plants Hydrolysates can Act on Delta Opioid Receptors

The inventors first discovered the ability of several peptides and plant proteins hydrolysate to act as antagonists or agonists of the DOR (delta opioid receptors). One hexapeptide YPLDLF (SEQ ID No 1) gave excellent results as agonist with EC50=3.9 µM. The inventors demonstrated that either pure peptide or plant protein hydrolysate can bind and activate DOR.

2. In Simulated Aging Conditions, Opioid Receptors are Less Expressed in Skin. DOR Agonist Peptides can Reverse this Phenomenon.

At the skin level, the aging process is closely associated to an increased level of micro-inflammation in the skin (Giacomoni et al., 2005), due to accumulation of external aggressions (repeated mechanical stresses, UV irradiations, pollutants), and to the inability of skin cells to face these aggressions (lower detoxifying activity, lower level of cellular energy, lower cellular regeneration). This so-called "inflamm-aging" process generates feedback responses that results in visible signs of aging: wrinkles, loss of tone, dark circles, sagging, fine lines, and the like.

The inventors simulated aging conditions on reconstructed human epidermis (RHE) with a mix of cytokines. They discovered that in these 'aging' conditions, the level of expression of delta opioid receptor is reduced. As it is known from literature that opioid receptors control the differentiation processes of skin and generates a thin skin phenotype, they discovered one of the causes of aging: a lower expression of delta opioid receptor due to cytokines leads to a poorer differentiation of skin.

The inventors applied the peptide on RHE at different doses and discovered that the peptide YPLDLF (SEQ ID No 1) enables to reactivate the expression of delta opioid receptor in skin. Therefore, they discovered that this peptide can penetrate the skin and reverse the aging process due to cytokines.

3. DOR Agonist Peptides can Act on Delta Opioid Receptors and Leads to the Regulation of Several Deregulated Genetic Factors in Aged Skins.

To better understand the effect of peptides on delta opioid receptor, the inventors measured the expression level of 64 human genes on reconstructed human epidermis. These epidermises were either treated with nothing, with a mix of cytokines to simulate the aging process, or with the blend of cytokines plus different quantities of peptides. The inventors discovered that, in the presence of cytokines, the majority of the genes were deregulated as compared to the control condition: they were either over or under expressed. In the conditions with the peptide, almost all the genes were brought back to a normal level of expression. The inventor therefore discovered that DOR agonist peptides can act on delta opioid receptor and equalize the unwanted effects of aging conditions.

4. DOR Agonist Peptides Act on Delta Opioid Receptor and Leads to the Regulation of Several Deregulated Protein Factors in Aged Skins.

The inventors achieved the same experiment than for genes, but measured the level of expression of key proteins, which are known to be involved in the differentiation of skin. They discovered that, in the cytokine induced condition, these proteins were deregulated (over or under expressed). But, epidermis treated with the peptides recovered a normal expression of these protein markers. The inventors discovered that DOR agonist peptides can balance and regulate the level of expression of differentiation markers in aged skins.

5. DOR Agonists Act on Delta Opioid Receptor and Lead to the Activation of Melanin Pigmentation.

As melanin production is controlled by a G-protein coupled receptor (the MC1 receptor), the inventors had the idea to test the effect of the previously tested DOR agonists on human skin explants to see which effect it could have on skin pigmentation. After few days of incubation of these skin explants with the molecules, without any UV irradiation, they discovered that skin explants started to produce melanin and melanosomes in their melanocytes. The inventors discovered that DOR agonists can stimulate the production on pigments in skin. This result is very surprising because the receptor µ (MOR) is the receptor associated with pigmentation (Kauser et al, 2004).

6. DOR Agonist Peptides Act on Opioid Receptors and Lead to the Skin Regeneration.

The inventors tested a cream containing the previously tested DOR agonist peptide on human volunteers in double blind clinical trial versus a placebo. After several days of use, they discovered that the skin of volunteers was significantly improved in terms of moisturization, reduction of trans-epidermal water loss, smoothness and reduction of wrinkles depth. The inventors discovered that the use of DOR agonist peptides that act on opioid receptors can have clinical effects versus a placebo and enable to reverse signs of aging on human skin.

Therefore, the present invention relates to the use of DOR agonists that act on delta opioid receptor in cosmetic and dermocosmetic applications to
  prevent and reverse the signs of aging; and/or,
  refill wrinkles (anti-aging products for normal or mature skins); and/or,
  improve skin smoothness (body and face products); and/or,
  equalize unbalanced markers in stressed skins; and/or,
  normalize disturbed gene expression in skin cells; and/or,
  erase crow's feet wrinkles (eye contour products); and/or,
  recover skin moisturization; and/or,
  prevent trans epidermal water loss in skin and therefore prevent dehydration of skin; and/or,
  reactivate skin cells differentiation; and/or,
  stimulate pigmentation (self tanning, hair repigmentation, pre sun products, hair care); and/or,
  synergistically act on G-protein coupled pathways in skin cells.

A first aspect of the present invention relates to the use of a DOR ligand for stimulating pigmentation of skin and/or hair. It also relates to a cosmetic method for stimulating pigmentation of skin or hair, comprising applying to human skin and/or hair a composition comprising a DOR ligand. In particular, the skin is the body and/or face skin. In a more specific aspect, the present invention relates to a hair care product comprising a DOR ligand. In this context, the DOR ligand is the active agent. In a particular aspect, it can be the sole active agent. Alternatively, it can be combined with additional active agents. Non-exhaustive examples of such additional active agents include precursors of melanin synthesis, activators of tyrosinase expression and active compounds strengthening hair bubble. The DOR ligand can be a DOR agonist or a DOR antagonist. In a preferred embodiment, the DOR ligand is a DOR agonist.

In particular, the present invention relates to the use of a DOR agonist for preparing a cosmetic composition for self tanning, hair pigmentation or repigmentation, pre-sun or sun products, hair care product such as shampoo or hair-conditioning or to a cosmetic composition comprising a DOR agonist for self tanning, hair pigmentation or repigmentation, pre-sun or sun products, hair care product such as shampoo or hair-conditioning. The composition is for topical, intradermic, transdermic or subcutaneous application. More preferably, the composition is for topical administration, in particular on skin or hair. The cosmetic composition may include at least one cosmetic additive. In a particular aspect, it can be the sole active agent. Alternatively, it can be combined with additional active agents, for instance as detailed above.

The DOR agonist may be a peptide or a non peptide molecule. For instance and non-exhaustively, it may be selected from the group consisting of rubiscolin-6 and its derivatives, deltorphin and its derivatives, Leu-enkephalin, Met-enkephalin, DPDPE (D-Penicillamine(2,5)-enkephalin) and its derivatives, DSLET, biphalin, JOM-13, DTLET, DSTBULET, BUBU, BUBUC and non peptide agonists such as BU-48, BW373U86, C-8813, 7-spiroindanyloxymorphone (SIOM), N-phenethyl-14-ethoxymetopon, ADL-5859, SNC-40, SNC-80, SNC-86, SNC-162, DPI-221, DPI-287, DPI-3290, TAN-67, RWJ-394,674, and norbuprenorphine.

In a preferred embodiment, the DOR agonist is selective for delta opioid receptor. By selective is intended that the DOR agonist has a lower IC50 for delta receptor than for mu or kappa receptor. In particular, the ratio of IC50 for mu and/or kappa by IC50 for delta is more than 1, preferably more than 10, still more preferably more than 30. The selective DOR agonist can be a peptide agonist or a non-peptide agonist. For instance, it may be selected from the group consisting of BU-48, SNC-80, C-8813, DPI-287, DPI-221, TAN-67, BW373U86, SIOM, RWJ-394,674, rubiscolin-6 and its derivatives, deltorphin and its derivatives, DPDPE, DSLET, JOM-13, DSTBULET, BUBU, and BUBUC.

The peptide sequences defined herein use the one letter code as following: A: Ala (alanine); R: Arg (arginine); N: Asn (asparagine); D: Asp (aspartic acid); C: Cys (cysteine); Q: Gln (glutamine); E: Glu (glutamic acid); G: Gly (glycine); H: His (histidine); I: Ile (isoleucine); L: Leu (leucine); K: Lys (lysine); M: Met (methionine); F: Phe (phenylalanine); P: Pro (proline); S: Ser (serine); T: Thr (threonine); W: Trp (tryptophan); Y: Tyr (tyrosine); V: Val (valine).

By "derivatives" is intended herein a peptide with substitutions, deletions or additions of 1, 2, 3, 4, or 5 amino acids and/or a peptide with modifications as detailed below, but which retains the DOR agonist activity or has a DOR agonist activity. Preferably, the substitutions are conservative, meaning the residue is substituted by an amino acid of the same physicochemical group. The physicochemical groups are generally defined as following: the non-polar or hydrophobic amino acids including A, V, I, L, P, F, M, and W, but more narrowly the non-aromatic hydrophobic amino acids as including A, V, I, L, P, and M; the uncharged polar group including G, S, T, C, Y, N and Q; the negatively charged polar group including E and D; and the positively charged polar group including R and K. Alternatively, the substitution may also be non-conservative. The derivative may also so comprise non-naturally-occurring amino acid such as azetidinecarboxylic acid, 2-aminoadipic acid, 3-aminoadipic acid, beta-alanine, aminopropionic acid, 2-aminobutyric acid, A-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

In a preferred embodiment, the peptide derivative comprises no more than 10, 9, 8, 7 or 6 amino acids, or has 5, 6, 7, 8, 9 or 10 amino acids.

The peptide bonds can be optionally modified in order to prevent proteolysis. For instance, at least peptide bond may be replaced by a bond selected for the group consisting of (—CH$_2$—NH—), (—NH—CO—), (—CH$_2$—O—), (—CH$_2$—S—), (—CH$_2$—CH$_2$—), (—CO—CH$_2$—), (—CHOH—CH$_2$—), (—N═N—), and (—CH═CH—). Optionally, all the peptide bonds are replaced.

The DOR agonist peptides may present substitutions, and enzymatic and/or chemical modifications. In particular, the modifications may be the substitutions of all or some of residues from L amino acid to D amino acid. In a very particular aspect, the peptides only comprise D amino acids. The peptides may be acetylated, conjugated to a lipid, esterified, glycosylated, amidated, and/or cyclized.

In particular, the DOR agonist peptides may be conjugated to a lipid in order to facilitate entry across the stratum corneum. In a particular embodiment, the peptides according to the invention can present a (or several) lipid moiety (moieties), covalently or not covalently attached. The lipid moiety (moieties) can be any lipid presenting from C3 to C20 carbon atoms, preferably linked at N- or C-terminal extremity. Preferably, the lipid is conjugated at the N-terminal end of the peptide. Alternatively, the lipid is conjugated at its C-terminal end. Non-exhaustive examples of lipids include, but are not limited to acetic acid, butyric acid, capronic acid, caprylic acid, caprynic acid, lauric acid, myristic acid, palmitic acid, stearic acid, arachidic acid, behenic acid, lignoceratic acid, palmitolic acid, oleic acid, linoleic acid, γ-linoleic acid, α-linoleic acid, eicosadinoic acid, eicosatrinoic acid, arachidonic acid, eicosapentaenoic acid, docosapentaeoic acid, and docosahexaenoic acid. For instance, the peptide may be palmitoylated. However, it can be noted that an advantage of rubiscolin-6 and its derivatives is their ability to penetrate the skin without any modification.

Alternatively, the DOR agonist peptides may comprise a moiety facilitating the cellular entry of the DOR agonist peptides. For instance, this moiety is well-known in the art (see for instance, Vives et al, 2008).

The DOR agonist peptides may be isolated from a natural source or can be synthesized.

Deltorphin and its derivatives include deltrophin (Y-$_D$M-FHLMD-NH$_2$ (SEQ ID No 2)) and derivatives such as the following peptides: Y-$_D$A-FDVVG-NH$_2$ (SEQ ID No 3, deltorphin I), Y-$_D$A-FEVVG-NH$_2$ (SEQ ID No 4, deltorphin II), and Y-$_D$L-FADVASTIGDFFHSI-NH$_2$ (SEQ ID No 5, Leu-deltorphin).

In the most preferred embodiment, the DOR selective agonist is rubiscolin-6 and its derivatives. Rubiscolin-6 has the sequence YPLDLF (SEQ ID No 1).

Rubiscolin-6 and its derivatives include peptides which have or comprise the sequence of formula (I)

(I)

Y-P-X1-D-X2-X3 (SEQ ID No 6)

wherein

X1 being a non-aromatic hydrophobic amino acid, preferably selected from the group consisting of L, I, M, V and A, more preferably selected from the group consisting of L, I, and M;

X2 being a non-aromatic hydrophobic amino acid, preferably selected from the group consisting of L, I, and M, more preferably selected from the group consisting of L and I;

X3, present or absent, being a hydrophobic amino acid, preferably selected from the group consisting of F, L, I, M, V and A, more preferably selected from the group consisting of F, I, and V, and in particular being F or V.

Therefore, Rubiscolin-6 and its derivatives may be a peptide selected from the group consisting of or a peptide comprising a sequence selected in the group consisting of YPLDLF (SEQ ID No 1), YPIDLF (SEQ ID No 7), YPMDLF (SEQ ID No 8), YPLDIF (SEQ ID No 9), YPLDLL (SEQ ID No 10), YPLDLI (SEQ ID No 11), YPLDLM (SEQ ID No 12), YPLDLV (SEQ ID No 13), YPLDLA (SEQ ID No 14), YPIDLV (SEQ ID No 15), YPMDLV (SEQ ID No 16), YPLDIV (SEQ ID No 17), YPIDIV (SEQ ID No 18), YPMDIV (SEQ ID No 19), YPIDLV (SEQ ID No 20), YPIDMV (SEQ ID No 21), YPIDII (SEQ ID No 22), YPMDII (SEQ ID No 23), YPMDL (SEQ ID No 24), YPIDL (SEQ ID No 25), and YPMDI (SEQ ID No 26). In a preferred embodiment, rubiscolin-6 and its derivatives may be a peptide selected from the group consisting of YPLDLF (SEQ ID No 1), YPIDLF (SEQ ID No 7), YPMDLF (SEQ ID No 8), and YPMDL (SEQ ID No 24). In a very specific embodiment, the DOR agonist is a peptide YPLDLF (SEQ ID No 1) or a peptide comprising the sequence YPLDLF (SEQ ID No 1), optionally modified as described above.

In a second aspect, the present invention relates to a cosmetic composition for topical, intradermic, transdermic or subcutaneous administration, preferably topical administration, comprising a peptide selected from rubiscolin-6 and its derivatives and at least one cosmetic additive. Rubiscolin-6 and its derivatives are as detailed above. It further relates to the use of a peptide selected from rubiscolin-6 and its derivatives for the preparation of a cosmetic composition for topical, intradermic, transdermic or subcutaneous administration, preferably topical administration. Preferably, the cosmetic composition is for preventing and/or reversing the sign of skin aging, and/or refilling wrinkles, improving skin smoothness, and/or equalizing unbalanced markers in stressed skin, and/or normalizing disturbed gene expression in skin cells, and/or erasing crow's feet wrinkles, and/or recovering skin moisturization, and/or preventing trans-epidermal water loss in skin, and/or reactivating skin cells differentiation, and/or stimulating pigmentation. In particular, the skin is the body or face skin. It also relates to a cosmetic method for preventing and/or reversing the sign of skin aging, and/or refilling wrinkles, improving skin smoothness, and/or equalizing unbalanced markers in stressed skin, and/or normalizing disturbed gene expression in skin cells, and/or erasing crow's feet wrinkles, and/or recovering skin moisturization, and/or preventing trans-epidermal water loss in skin, and/or reactivating skin cells differentiation, and/or stimulating pigmentation, comprising applying to human skin and/or hair a composition comprising a peptide selected from rubiscolin-6 and its derivatives. In this context, the DOR agonist peptide is the active agent. In a particular aspect, it can be the sole active agent. Alternatively, it can be combined with additional active agents. In particular, such additional active agents may be anti-ageing agents, photo-protective agents, an antioxidant and anti-glycation agents.

Rubiscolin-6 and its derivatives can be used for normalizing skin barrier, restructuring mature skins, smoothing skin surface and/or refilling deep wrinkles. Therefore, their applications can be eye care products, in particular eye contour, eye gel, under eye serum), products for the treatment of expression lines, anti-aging products for the reduction of deep wrinkles, face care products for mature skins, neck care products, restructuring body care products, and protection from daily aggressions. In the cosmetic composition of the present invention, the DOR agonist is added in a cosmetically effective amount. The amount may vary depending on the condition to treat, the age, the severity of the condition to treat, the duration of the treatment, and the like. In a particular embodiment, at the cosmetically effective amount, the DOR agonist does not have any therapeutic effect. Indeed, the uses contemplated herein are non-therapeutic uses.

Typically, when the DOR agonist is rubiscolin-6 and one of its derivatives, the composition may comprise between 0.000005-0.002% in weight of the peptide with respect to the total weight of the composition, preferably between 0.00001% and 0.001%, still more preferably between 0.00003% and 0.0006%. When expressed in ppm, the composition typically comprises from 0.05 to 20 ppm of peptide, preferably from 0.1 to 10 ppm, still more preferably from 0.3 to 6 ppm.

The cosmetic composition may be formulated as a cream, a gel, a moisturizer, a lotion, a milk, an oil, an ointment, a wax, a mousse, a paste, a serum, a pomade, a hair care product, or a shampoo. It may optionally be applied in the form of an aerosol. It may also be in solid form, such as in the form of a stick. It may be used as a care product and/or as a makeup product for the skin.

The cosmetic additives may be added to achieve a desired cosmetic result. Desired cosmetic results may be determined by one of ordinary skill in the art or the user of the disclosed compositions. Cosmetic additives may include, but are not limited to, carriers, excipients, vehicle ingredients, moisturizers, humectants, cosmetic salts, adjuvants, oils, emulsifiers, co-emulsifiers, gelling agents, absorbers, solvents, photoprotective agents, and inert bases.

The compositions useful for topical application may contain additional ingredients such as carrier, excipient, or vehicle ingredients such as, for example, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments which are non-toxic and pharmaceutically or dermatologically acceptable. Additionally, moisturizers or humectants can be added to the present compositions if desired. Examples of such additional ingredients can be found in Remington's Pharmaceutical Sciences, Eighteenth Edition, A. R. Gennaro, Ed., Mack Publishing Co., Easton, Pa., 1990.

This cosmetic composition may be in any presentation form normally used in cosmetics, and it may, for example, be in the form of an optionally gelled aqueous solution, a dispersion of the lotion type, optionally a two-phase lotion, an emulsion obtained by dispersing a fatty phase in an aqueous phase (OAV emulsion) or conversely (W/O emulsion), a triple emulsion (W/O/W or 0/W/O emulsion), nanoemulsions, in particular O/W nanoemulsions, in which the size of the drops is less than 100 nm; or a vesicular dispersion of ionic and/or nonionic type. These compositions are prepared according to the usual methods. In one embodiment, a composition in the form of an oil-in-water emulsion is used. In one aspect, the DOR agonist peptides can be prepared in specific conditions such as included in liposomes, niosomes, nanosomes, nanospheres or nanocapsules.

For local application to the hair or the scalp, the cosmetic composition may be in the form of aqueous, alcoholic or aqueous-alcoholic solutions; in the form of creams, gels, emulsions or mousses; in the form of aerosol compositions also comprising a propellant under pressure.

When the composition is in aqueous form, especially in the form of an aqueous dispersion, emulsion or solution, it may comprise an aqueous phase, which may comprise water, a floral water and/or a mineral water.

In a known manner, the cosmetic composition disclosed herein may also comprise at least one adjuvant chosen from adjuvants that are common in cosmetics, such as hydrophilic and lipophilic gelling agents, hydrophilic and lipophilic active agents, preserving agents, antioxidants, solvents, fragrances, fillers, screening agents, pigments, odor absorbers and dyestuffs. The at least one adjuvant is present in an amount ranging, for example, from 0.01% to 20% by weight relative to the total weight of the composition. Depending on its nature, the at least one adjuvant may be introduced into the fatty phase, into the aqueous phase, or into lipid vesicles. In any case, these adjuvants, and also the proportions thereof, will be chosen so as not to harm the desired properties of the combination of anti-wrinkle active agents disclosed herein.

When the cosmetic composition disclosed herein is an emulsion, the proportion of the fatty phase may range from 5% to 80% by weight such as from 5% to 50% by weight relative to the total weight of the composition. The oils, emulsifiers and co-emulsifiers used in the cosmetic composition in emulsion form are chosen from those conventionally used in the field under consideration. The emulsifier and co-emulsifier are present in the composition in an amount ranging from 0.3% to 30% by weight such as from 0.5% to 20% by weight relative to the total weight of the composition.

As oils which may be used in this disclosure, mention may be made, for example, of mineral oils (liquid petroleum jelly or hydrogenated polyisobutene), oils of plant origin (avocado oil or soybean oil), oils of animal origin (lanolin), silicone oils (cyclomethicone or dimethicone) and fluoro oils (perfluoropoly ethers). Fatty alcohols (cetyl alcohol), fatty acids and waxes (carnauba wax or ozokerite) may also be used as fatty substances.

As examples of emulsifiers and co-emulsifiers that may be used herein, mention may be made, for example, of fatty acid esters of polyethylene glycol such as PEG-100 stearate, and fatty acid esters of glycerol such as glyceryl stearate.

Hydrophilic gelling agents that may be included are, for example, carboxyvinyl polymers (carbomer), acrylic copolymers such as acrylate/alkylacrylate copolymers, polyacrylamides, such as crosslinked polyacrylamido-methylpropanesulphonic acid, polysaccharides, natural gums and clays, and lipophilic gelling agents that may be mentioned include, for example, modified clays, such as bentones, metal salts of fatty acids, hydrophobic silica and poly ethylenes.

In one embodiment, the hydrophilic gelling agent for the composition disclosed herein is chosen from a crosslinked polyacrylamido-methylpropane-sulphonic acid as described in EP 0850642, WO9800094 or the Hostacerin AMPS commercialized by Clariant.

In an addition aspect, the present invention relates to a device comprising a peptide selected from rubiscolin-6 and its derivatives, the device being capable of delivering said peptide via intraepidermal and/or intradermal and/or subcutaneous injection. The said device may be, for example, a syringe with a needle or an injection device without a needle, such as those used in the care technique known as mesotherapy. A kit comprising a device may also be envisaged, the said kit comprising a device, in particular a syringe or an injection device, and the DOR agonist, in particular rubiscolin-6 and its derivatives, as defined above. The said kit may also comprise a needle. The said device may be in ready-to-use form, i.e. prefilled, or may need to be filled before use. In the latter case, a composition or another device (such as a vial) comprises the DOR agonist, in particular rubiscolin-6 and its derivatives, as defined above, optionally in combination with at least one other active compound. Alternatively, the composition of the invention may be used in combination with laser treatment which improves the composition penetration.

The composition of the invention may also be used in combination with other treatments such as the light therapy or phototherapy, in particular such as Low-level laser therapy or Deep penetrating light therapy. In addition, the topical application of the composition can be combined with the use of a facial massager.

The following are examples provided solely to illustrate the present invention and are not intended to limit the scope of the invention, as described herein.

EXAMPLES

Example 1

Experiments

1. Test of Peptides and Proteins Hydrolysates on Delta Opioid Receptors

Frozen spinach leaves were thawed and disrupted in fine particles a blender. This juice was further treated with ultrasounds to disrupt cells and proteins were recovered by acidic precipitation. These proteins were then digested by several enzymes, including pepsin and papain. The hydrolysate was purified (ultrafiltration), fractionated and stored before testing. Meanwhile, synthetic peptides were ordered from a manufacturer. The peptides and the hydrolysates were tested on cells bearing the delta2 opioid receptor and cell impedance was measured to evaluate the binding activity of the tested compounds (Law and Loh, 1993).

The results were expressed as a percent of control specific agonist response (DPDPE (SEQ ID No 27) was used for this purpose) ((measured specific response/control specific agonist response)×100) obtained in the presence of the test compounds.

The EC50 values (concentration producing a half-maximal specific response) and IC50 values (concentration causing a half-maximal inhibition of the control specific agonist response) were determined by non-linear regression analysis of the concentration-response curves generated with mean replicate values using Hill equation curve fitting (Y=D+[(A D)/(1+(C/C50)nH)], where Y=specific response, D=minimum specific response, A=maximum specific response, C=compound concentration, and C50=EC50 or IC50, and nH=slope factor).

TABLE 1

| EC50 determination | | |
|---|---|---|
| Compound | EC50 | Flags |
| YP | | N.C. |
| YPL | | N.C. |
| YPLD | | N.C. |
| YPLDL | | >1.0 10$^{-5}$ |
| YPLDLF | 3.9 10$^{-6}$M | |
| 02.01 PEPS | 0.87% (v/v) | |
| 02.02 PEPS | | >5% (v/v) |
| 02.01 PANE | | N.C. |
| 02.02 PANE | | N.C. |

YP, YPL, YPLD (SEQ ID No 29), YPLDL (SEQ ID No 28), YPLDLF (SEQ ID No 1): pure peptides
PEPS: fractions of proteins hydrolyzed with pepsin
PANE: fractions of proteins hydrolyzed with papain.
N.C.: EC50 value not calculable. Concentration-response curve shows less than 25% effect at the highest tested concentration.
>: EC50 value above the highest test concentration. Concentration-response curve shows less than 50% effect at the highest tested concentration This experiment (Table 1 and FIG. 1) revealed that one peptide was functionally active on DOR as a ligand with an EC50=3.9 µM. One protein hydrolysate was also active on DOR, showing that not only pure peptides, but also protein hydrolysates could be active as ligand of DOR.

2. Effect of Cytokines on the Expression Level of DOR in Epidermis

The protein expression of the opioid receptor delta (DOR) was analyzed using a "tissue microarray" (TMA) composed of numerous skin-related cellular models in order to identify the best models for further studies.

Paraffin Embedding

Formaldehyde-fixed tissues were dehydrated in multiple baths with increasing concentration of ethanol and then embedded in "Paraplast X-tra" paraffin. The transversal sections were carried out using a microtome (5 µm thickness) and kept at room temperature until staining.

Immunohistochemical Labeling

The sections were deparaffinized then the antigenic sites were retrieved using specific buffers (pH6 and pH9). The sections were then washed and incubated with hydrogen peroxide. After an additional washing step, the sections were incubated with the primary antibody (anti-DOR). The labeling was then revealed using a biotin-conjugated secondary antibody. After peroxidase-conjugated streptavidine and peroxidase substrate addition, nuclei were counter-stained with a solution of haematoxylin. The slices were washed in ultra-pure water and mounted in aqueous medium.

Microscopic Observation

Sections were observed using a NIKON E400 microscope. Images were captured with a NIKON DS-Ri1 and processed with NIS-Elements 3.10 software.

TABLE 2

Analysis of the expression of DOR in epidermis

| | |
|---|---|
| FIG. 2A: Normal human skin - epidermis and dermis | The expression of protein DOR was observed in the granular layer of the epidermis. Moreover, some dermal cells were slightly labeled in their cytoplasm. |
| FIG. 2B: Normal human skin - dermis and sebaceous glands | Some zones of the sebaceous gland expressed protein DOR |
| FIG. 2C: Reconstructed human epidermis (RHE) | Protein DOR was strongly expressed in RHE granular layer cell membranes. All the living cells of the basal and supra-basal layers expressed the protein in their cytoplasm. |
| FIG. 2D: RHE treated with PMA at 2 µg | Compared to the non-treated RHE, the expression of DOR was decreased after Phorbol myristate acetate(PMA) treatment at 2 µg. No more labeling was observed in the spineous layer while the expression persisted strongly in the basal layer and slightly in the granular layer. |
| FIG. 2E: RHE treated with mix of cytokines (IL-17 + OSM + TNF-α) | Compared to the non-treated RHE, the expression was strongly decreased in the RHE treated with the mix of cytokines: in the granular and spineous layer labeling was totally vanished. Only the expression in the basal layer was conserved. |

These results (Table 2 and FIG. 2) showed that protein DOR was expressed in the human skin and in the 3D model of reconstructed human epidermis. The expression was really important in the granular layer of both models. After inflammation treatments (mix of cytokines or PMA) simulating aged skin conditions, the expression of the DOR protein decreased or totally disappeared. This demonstrates that in aging conditions, the delta opioid receptors are less expressed.

3. Anti-Cytokines Effect of a DOR Agonist Peptide on the Expression Level of DOR in the Epidermis In the present study, the effects of a peptide (YPLDLF, SEQ ID No 1) on the expression of opioid receptor delta (DOR) were researched on a reconstructed human epidermis (RHE) model under basal or stimulated conditions. More precisely, the RHE were stimulated by a mix of cytokines (IL-17+OSM+TNF-α) able to induce a strong inflammatory profile and a psoriatic phenotype in keratinocytes.

Reconstructed human epidermis (RHE) of 11 days old was prepared according to a derived method described by Poumay et al. (2004). These RHE were cultivated at 37° C. and 5% of $CO_2$ in a specific maintenance medium.

The RHE treated under basal conditions were placed in assay medium containing or not (non-stimulated control) the peptide solutions and incubated for 54 hours. For inflammatory conditions, the RHE were placed in assay medium containing or not (stimulated control) the peptide solutions or the reference OAK inhibitor I at 10 µM) and pre-incubated for 6 hours. The RHE were then stimulated with a mix of cytokines (IL-17+OSM+TNF-α at 3 ng/ml) and incubated for 48 hours. All experimental conditions were performed in n=3.

At the end of incubation, the supernatants were collected and the RHE were washed in phosphate buffered saline solution (PBS) for immunohistofluorescence analysis.

Paraffin Embedding

Formaldehyde-fixed tissues were dehydrated in multiple baths with increasing concentration of ethanol and then embedded in paraffin. The transversal sections were carried out using a microtome (5 µm thickness) and kept at room temperature until staining.

Immunohistochemical Labeling

The sections were deparaffinized and the antigenic sites were retrieved using specific buffer (pH6). The sections were then washed and incubated with hydrogen peroxide. After an additional washing step, the sections were incubated with the primary antibody (anti-OPRD). The labeling was then revealed using a biotin-conjugated secondary antibody. After peroxidase-conjugated streptavidine and peroxidase substrate addition, nuclei were counter-stained with a solution of haematoxylin. The sections were washed in ultra-pure water and mounted in aqueous medium.

Microscopic Observation

Sections were observed using a NIKON E400 microscope. Images were captured using a NIKON DS-Ri1 and processed with NIS-Elements 3.10 software.

Results

TABLE 3

"Scoring" of DOR1 expression in RHE under different conditions

| No cytokines Control | Stimulated conditions with 3 ng/ml of cytokines | | | | |
|---|---|---|---|---|---|
| | Control | JAK inhibitor I | Peptide at 0.03 PPM | Peptide at 0.3 PPM | Peptide at 3 PPM |
| ++ | − | ++ | ++ | ++ | ++ |

Protein DOR was correctly detected in the reconstructed human epidermis following in situ immunohistolabeling. DOR1 was strongly and almost exclusively expressed in the granular layer. Following treatment with the cytokine mix, the expression of DOR1 in the stimulated control was strongly decreased compared to the non-stimulated control. The anti-inflammatory reference JAK inhibitor I, tested at 10 µM, reversed the inhibitory effect of the cytokine mix on OPRD1 expression. The inhibitory effect of the cytokine mix on OPRD1 expression was also reversed following treatment with the peptide.

This experiment demonstrated that a DOR agonist peptide, like the YPLDLF (SEQ ID No 1) peptide, can reverse the effect of a mix of cytokines on the level of expression of DOR.

4. Effects of a Peptide on Gene Expression in Inflammatory Reconstructed Human Epidermis Transcriptional effects of a peptide (YPLDLF, SEQ ID No 1) on gene expression were researched on a reconstructed human epidermis (RHE) model under inflammatory conditions. The inflammation of the RHE was induced using a mix of cytokines (IL-17+OSM+TNF-α). The effects on gene expression were evaluated using RT-qPCR technology. Extracted mRNA was analyzed on a customized PCR array designed by the study sponsor and containing 64 target genes (including 2 housekeeping genes) selected for their role in keratinocyte differentiation, or their involvement in cell junctions and lipid synthesis, or their relation to opioid receptor delta (DOR).

Reconstructed human epidermis (RHE) of 11 days old was prepared according to a derived method described by Poumay et al. (2004). These RHE were cultivated at 37° C. and 5% of $CO_2$ in a specific maintenance medium.

The RHE were cultured in assay medium containing or not (controls) the test compounds or the reference OAK inhibitor I at 10 μM) and pre-incubated for 24 hours. Epidermises were then stimulated or not (non-stimulated control) with a cytokine mix (IL-17+OSM+TNF-α) at 3 ng/ml and the epidermises were incubated for 24 hours. All experimental conditions were performed in n=2.

At the end of incubation, the supernatants were collected and the RHE were washed in phosphate buffered saline solution (PBS) and immediately dry-frozen at −80° C.

Differential Expression Analysis

The expression of markers was analyzed using RT-qPCR method on mRNA extracted from RHE for each treatment (before RNA extraction the replicates were pooled).

Analysis of gene expression was performed in n=2 using a customized PCR array dedicated to research and adapted to 'screening' format.

Reverse Transcription

Total RNA was extracted from each sample using TriPure Isolation Reagent® according to the supplier's instructions. The amount and quality of RNA were evaluated using a lab-on-a-chip Bioanalyzer (Agilent technologies). The RNA quality controls are presented in appendix. Potential contaminant traces of genomic DNA were removed using the DNAfree system (Ambion). The reverse-transcription of mRNA was conducted in presence of oligo(dT) and Superscript II reverse-transcriptase. Quantification of cDNA was performed using Nanovue (GE Healthcare) and adjustment of cDNA at 10 ng/μl.

Quantitative PCR

The PCRs (Polymerase Chain Reactions) were performed using the <<LightCycler®>> system (Roche Molecular System Inc.) according to supplier's instructions. This system allows rapid and powerful PCRs, after determining analysis conditions of the test primers.

The reaction mix (10 μl final) was added as follows:
2.5 μl of cDNA at 10 ng/μl,
primers forward and reverse,
reagent mix containing taq DNA polymerase, SYBR Green I and MgCl2.

Data Management of Quantitative PCR

Raw data were analyzed with Microsoft Excel® software.

The incorporation of fluorescence in amplified DNA was continuously measured during the PCR cycles. This resulted in a "fluorescence intensity" versus "PCR cycle" plot allowing the evaluation of a relative expression (RE) value for each marker. The value selected for RE calculations is the "output point" (Ct) of the fluorescence curve. For a considered marker, the highest is the cycle number; the lowest is the mRNA quantity. The RE value was expressed in arbitrary units (AU) according to the formula: $(\frac{1}{2}^{number\ of\ cycles}) \times 10^6$.

Results

The Peptide, tested at 0.3 μg/ml, showed overall a modulation of gene expression profile of cytokine mix-stimulated RHE.

This experiment demonstrated that DOR agonist peptides, like the YPLDLF (SEQ ID No 1). peptide, can reverse the deregulating effect of a mix of cytokines on the level of expression specific genes in the epidermis.

TABLE 4

| expression analysis | | | | |
|---|---|---|---|---|
| Relative expression of genes versus the control conditions (non stimulated RHE) | | | With cytokines % Control | With cytokines and peptide 0.3 PPM (Mean HK) |
| Function of the genes | Ref of genes | Name of the proteins | 100 | 100 |
| Housekeeping | RPS28 | Ribosomal protein S28 | 104 | 91 |
| | GAPDH | Glyceraldehyde-3-phosphate dehydrogenase | 94 | 116 |
| Opioid receptor delta 1 related markers | OPRD1 | Opioid receptor, delta 1 | 97 | 101 |
| | ADRB2 | Adrenergic, beta-2-, receptor, surface | 62 | 259 |
| | CREB1 | cAMP responsive element binding protein 1 | 120 | 109 |
| | GNAS | GNAS complex locus | 121 | 130 |
| | MAPK1 | Mitogen-activated protein kinase 1 | 126 | 108 |
| | MAPK14 | Mitogen-activated protein kinase 14 | 117 | 109 |
| | PTGS2 | Prostaglandin-endoperoxide synthase 2 (prostaglandin G/H synthase and cyclooxygenase) | 42 | 119 |
| | STAT3 | Signal transducer and activator of transcription 3 (acute-phase response factor) | 444 | 120 |
| | BIRC5 | Baculoviral IAP repeat-containing 5 | 25 | 88 |
| | ODC1 | Ornithine decarboxylase 1 | 52 | 110 |

TABLE 4-continued expression analysis

| | | Relative expression of genes versus the control conditions (non stimulated RHE) | With cytokines % Control (Mean HK) | With cytokines and peptide 0.3 PPM |
|---|---|---|---|---|
| | CASP3 | Caspase 3, apoptosis-related cysteine peptidase | 117 | 104 |
| | SLC1A3 | Solute carrier family 1 (glial high affinity glutamate transporter), member 3 | 39 | 100 |
| | EGFR | Epidermal growth factor receptor (erythroblastic leukemia viral (v-erb-b) oncogene homolog, avian) | 138 | 141 |
| Keratinocyte differentiation | CALML5 | Calmodulin-like 5 | 57 | 72 |
| | FLG | Filaggrin | 34 | 117 |
| | KRT1 | Keratin 1 | 27 | 140 |
| | KRT10 | Keratin 10 | 26 | 145 |
| | LOR | Loricrin | 60 | 121 |
| | SPRR1A | Small proline-rich protein 1A | 181 | 142 |
| | SPRR1B | Small proline-rich protein 1B (cornifin) | 251 | 127 |
| | SPRR2A | Small proline-rich protein 2A | 467 | 111 |
| | TGM1 | Transglutaminase 1 (K polypeptide epidermal type I, protein-glutamine-gamma-glutamyltransferase) | 308 | 108 |
| | CRNN | Cornulin | 55 | 71 |
| | IVL | Involucrin | 90 | 119 |
| | KRT19 | Keratin 19 | 112 | 134 |
| | PADI1 | Peptidyl arginine deiminase, type I | 19 | 105 |
| | SFN | Stratifin | 173 | 143 |
| Gap Junctions | GJA1 | Gap junction protein, alpha 1, 43 kDa | 46 | 111 |
| | GJA5 | Gap junction protein, alpha 5, 40 kDa | 100 | 90 |
| | GJB2 | Gap junction protein, beta 2, | 405 | 131 |
| | GJB3 | Gap junction protein, beta 3, 31 kDa | 73 | 111 |
| | GJB4 | Gap junction protein, beta 4, 30.3 kDa | 89 | 77 |
| | GJB5 | Gap junction protein, beta 5, 31.1 kDa | 78 | 122 |
| | GJB6 | Gap junction protein, beta 6, 30 kDa | 197 | 203 |
| | GJC1 | Gap junction protein, gamma 1, 45 kDa | 96 | 126 |
| | GJD3 | Gap junction protein, delta 3, 31.9 kDa | 108 | 487 |
| | PANX1 | Pannexin 1 | 190 | 133 |
| Tight junctions | CLDN1 | Claudin 1 | 93 | 128 |
| | CLDN2 | Claudin 2 | 72 | 121 |
| | OCLN | Occludin | 143 | 131 |
| | F11R | F11 receptor | 174 | 115 |
| | TJP1 | Tight junction protein 1 (zona occludens 1) | 162 | 129 |
| | TJAP1 | Tight junction associated protein 1 (peripheral) | 87 | 81 |
| Adherens junction | CDH1 | Cadherin 1, type 1, E-cadherin (epithelial) | 173 | 126 |
| | CTNNA1 | Catenin (cadherin-associated protein), alpha 1, 102 kDa | 132 | 117 |
| | CTNNB1 | Catenin (cadherin-associated protein), beta 1, 88 kDa | 93 | 134 |
| | PVRL1 | Poliovirus receptor-related 1 (herpesvirus entry mediator C) | 140 | 131 |
| | DST | Dystonin | 38 | 93 |
| | CDSN | Corneodesmosin | 115 | 161 |
| | DSG1 | Desmoglein 1 | 75 | 98 |
| | DSP | Desmoplakin | 151 | 107 |
| | EPPK1 | Epiplakin 1 | 99 | 82 |
| | EVPL | Envoplakin | 107 | 132 |
| | ITGAV | Integrin, alpha V (vitronectin receptor, alpha polypeptide, antigen CD51) | 292 | 103 |
| | ITGB3 | Integrin, beta 3 (platelet glycoprotein IIIa, antigen CD61) | — | — |
| | ITGA2 | Integrin, alpha 2 (CD49B, alpha 2 subunit of VLA-2 receptor) | 131 | 108 |
| Lipid synthesis | ACSS2 | Acyl-CoA synthetase short-chain family member 2 | 94 | 113 |
| | GBA | Glucosidase, beta; acid (includes glucosylceramidase) | 112 | 110 |
| | SMPD1 | Sphingomyelin phosphodiesterase 1, acid lysosomal | 88 | 87 |
| | SPTLC1 | Serine palmitoyltransferase, long chain base subunit 1 | 92 | 120 |
| | SULT2B1 | Sulfotransferase family, cytosolic, 2B, member 1 | 92 | 173 |
| | UGCG | UDP-glucose ceramide glucosyltransferase | 119 | 117 |

5. Proteins

In the present study, the effects of a peptide on the expression of 7 proteins were assessed on a reconstructed human epidermis (RHE) model stimulated or not with a mix of cytokines (IL-17+OSM+TNF-α).

More precisely, effects of compounds were evaluated on the protein expression of markers involved in:
- tight junctions (Occludin),
- adherens junctions (Corneosdesmosin)
- keratinocyte differentiation (keratin 10, involucrin, calmodulin-like5),
- and lipid synthesis (Acyl-CoA synthetase and sulfotransferase 2B).

Reconstructed human epidermis (RHE) of 11 days old were prepared according to a derived method described by Poumay et al. (2004). These RHE were cultivated at 37° C. and 5% of $CO_2$ in a specific maintenance medium.

The RHE were treated with assay medium containing or not (control) the test compounds and incubated for 72 hours with a treatment renewal after 24 hours. All experimental conditions were performed in n=3.

At the end of incubation, the supernatants were collected and the RHE were washed in phosphate buffered saline solution (PBS) for in situ immunolabeling.

The RHE were treated with assay medium containing or not (control) the test compounds or the JAK inhibitor I at 10 μM and incubated for 24 hours. After pre-incubation, assay medium and treatments were renewed and epidermises were stimulated with a cytokine mix (OSM+IL-17+TNF-α*) at 3 ng/ml and incubated for additional 48 hours. All experimental conditions were performed in n=3.

*Oncostatin M (OSM)+Interleukin 17 (IL-17)+ Tumor necrosis factor alpha (TNF-α)

At the end of incubation, the supernatants were collected and the RHE were washed in phosphate buffered saline solution (PBS) for in situ immunolabeling.

Immunofluorescent labeling of Acetyl-coenzyme A synthetase, Corneodesmosin, Involucrin, Keratin 10, and Occludin.

After incubation, the RHE were snap-frozen in liquid isopentane/N2 and stored at −80° C. The transversal sections were carried out using a microtome (5 μm thickness, one slide per RHE, several sections per slide).

The sections were fixed with an acetone/methanol mix and dried. After PBS-milk 5% saturation, the sections were incubated with the specific primary antibody solutions. After washes, the binding sites were revealed using appropriate secondary coupled-antibody and the cell nuclei were stained with propidium iodide solution. The sections were washed and then observed under epifluorescence microscopy.

Immunoperoxydase Labeling of Calmodulin-Like 5 and Sulfotransferase Cytosolic 2b After incubation, RHE were rinsed and fixed with formaldehyde solution. Fixed tissues were dehydrated in multiple baths with increasing concentration of ethanol and then embedded in paraffin. The transversal sections were carried out using a microtome (5 μm thickness) and stored at room temperature.

The sections were deparaffinized then the antigenic sites were retrieved. The sections were washed and incubated with hydrogen peroxide. The sections, once washed, were incubated with the primary antibody (anti-Calmodulin-like 5 or anti-SULT2B1). After washing, the labeling was revealed using a biotin-conjugated secondary antibody. After peroxidase-conjugated streptavidine and peroxidase substrate addition, nuclei were counter-stained with a solution of haematoxylin. The sections were washed, mounted in aqueous medium and observed under transmitted-light microscopy.

Microscopic Observation and Image Analysis

Sections were observed using a NIKON E400 microscope. Images were captured with a NIKON DS-Ri1 and processed with NIS-Elements 3.10 software (3 pictures per replicate). The image analysis was performed by measuring the fluorescence intensity using Image J software.

Results were expressed in % of the level of expression of each protein maker in non treated RHE.

TABLE 5

Protein expression

| PROTEIN | ROLE IN SKIN | PROTEINS EXPRESSION LEVEL IN HUMAN EPIDERMIS (RHE) | | |
|---|---|---|---|---|
| | | Normal conditions | Stimulated conditions with cytokines | |
| | | | No peptide | 3 PPM peptide |
| Corneodesmosin | Barrier function (corneocytes) | 100% | 147% | 84% |
| Involucrin | Barrier function (cornified envelope) | 100% | 122% | 99% |
| Calmodulin like 5 | Homeostasis (Ca2+) | 100% | 40% | 100% |
| Occludin | Homeostasis (tight junctions) | 100% | 50% | 97% |
| Keratin 10 | Robustness (epidermis integrity) | 100% | 120% | 104% |
| Acyl-CoA synthetase | Energy production (mitochondria) | 100% | 33% | 65% |
| Sulfotransferase 2B | Lipids synthesis (cholesterol sulfate) | 100% | 200% | 100% |

This experiment demonstrated that DOR agonist peptides, like the YPLDLF (SEQ ID No 1) peptide, can normalize the deregulating effect of a mix of cytokines on the level of expression of specific proteins in the epidermis. Such compounds can therefore reverse unbalanced situations as it happens upon aging. More significantly, these compounds are regulating the expression of proteins involved in tight junctions (occluding), adherent junctions (corneodesmosin) and keratinocyte differentiation (keratin 10, involucrin, clamodulin like 5) and lipid (aceyl-coA synthetase and sulfotransferase 2B) synthesis in the skin. DOR agonist peptides, like the YPLDLF (SEQ ID No 1) peptide, can therefore have major effects in the reorganization of a proper metabolism of skin, and favor skin's restructuration.

6. Evaluation of the Pro-Pigmentation Properties DOR Agonist Peptides on Skin Explants This study aims to explore the pro pigmenting activity of an ingredient (peptide YPLDLF, SEQ ID No 1) on human skin explants maintained in survival.

The activity of the product was evaluated by:
- histological expertise of general morphology of the skin after Masson trichrome staining,
- a visualization of melanin by a silver impregnation.

Immunostaining of Melan-A

Skin explants with a diameter of 10 mm were prepared from plastic surgery skin sample from a 43 years old woman. The explants were placed in survival in a specific growth medium at 37° C. in a humid atmosphere enriched with 5% CO2.

The peptide solutions (at 0.3 PPM or 3 PPM) were applied topically for 2 hours every day using a filter paper discs presoaked in 30 µl of each solution.

Control explants did not receive any treatment except the renewal of the culture medium.

Some other control explants were irradiated daily with UV (+6 to 8% of UVB) at a dose of 1.12 J/cm2.

At D0, a T0 lot of the explants were removed and cut in half. One half was fixed in buffered formalin and the other half was frozen at −80° C. By day 6 and day 10, three explants from each batch were taken and treated in the same way.

The melanin was visualized by silver impregnation according to the technique of Masson Fontana variant. Labeled melanin has been evaluated by microscopic examination.

The expression of melanin in the basal layers, was quantified by image analysis using the software Cell-D.

Melan-A was a detected with a monoclonal antibody anti-Melan-A (from Santa Cruz company) for 1 h at room temperature with a RTU Vectastain Universal amplifier system VECTOR avidin/biotin and revealed by FITC. The cell nuclei were colored with a propidium iodide. Labeled Melan-A has been evaluated by microscopic examination and counting of melanocytes Melan-A positive and the results expressed per centimeter of epidermis.

TABLE 6

Semi-quantitative physiological changes in melanocytes from human skin explants UVA-irradiated or treated with the peptide solutions for 6 days.

| | Untreated Control | UVA irradiated | Peptide (0.3 ppm) | Peptide (3 ppm) |
|---|---|---|---|---|
| Melanin in melanocyte | + | ++ | + | ++ |
| Melanocyte dendricity | + | ++ | ++ | ++ |
| Melanocyte contact with keratinocyte | + | ++ | + | ++ |
| Melanin transfer to keratinocyte | + | ++ | + | ++ |

This experiment demonstrated that, surprisingly, a peptide that binds on opioid receptors can activate in a dose dependent manner the production of pigment (melanin) in human skin within 6 days. The efficiency of stimulation of melanin production and melanosomes creation by this peptide is almost as good as the effect of UV irradiation on the skin.

7. Double-Blind and Placebo-Controlled Clinical Evaluation of the Efficacy of an Anti-Wrinkle Cosmetic Product The aim of the study was to evaluate the efficacy of an anti-wrinkle cosmetic product in attenuating of the appearance of wrinkles, improving the skin surface and attenuating the signs of skin ageing. In order to reach this goal a clinical study was carried out on 20 volunteers. Product efficacy was evaluated 15, 30 and 60 days after daily product use by means of instrumental analysis technique as described here below. The analysis was then completed with both the clinical evaluation performed by the dermatologist and the self-assessment of the subjects participating in the study.

Skin surface is quantitatively assessed by Primos 3D (GFMesstechnik GmbH). Primos 3D is a non-contact in vivo skin measurement device based on structured light projection. In conjunction with a comprehensive 3-D measurement and evaluation software, the sensor allows to evaluate skin surface properties (i.e. wrinkle depth, volume, roughness etc.). In this study it is calculated the Rz parameter (ISO 4287, DIN 4768) and wrinkle depth.

The measurement of the skin moisture is based on the internationally recognized CORNEOMETER® method (Courage+Khazaka, electronic GmbH). This measurement is based on the dielectric constant of water. The probe shows changes of capacitance according to the moisture content of the measuring object. An electric scatter field penetrates the very first layer of the skin and determines the dielectricity.

Trans epidermal water loss is measured by means of the internationally recognized TEWAMETER® method. The instrument used is a Tewameter 300® (Courage+Khazaka, electronic GmbH).

Tested Creams:

PHN (placebo): AQUA, OCTYLDODECYL NEOPENTANOATE, OCTYLDODECANOL, MYRISTYL MYRISTATE, ACRYLATES/C10-30 ALKYL ACRYLATE CROSSPOLYMER, SODIUM HYDROXIDE, PHENOXYETHANOL, METHYLPARABEN, ETHYLPARABEN, BUTYLPARABEN, PROPYLPARABEN, ISOBUTYLPARABEN PHG (with 3 PPM of peptide YPLDLF, SEQ ID No 1): AQUA, OCTYLDODECYL NEOPENTANOATE, OCTYLDODECANOL, MYRISTYL MYRISTATE, ACRYLATES/C10-30 ALKYL ACRYLATE CROSSPOLYMER, SODIUM HYDROXIDE, PHENOXYETHANOL, METHYLPARABEN, ETHYLPARABEN, BUTYLPARABEN, PROPYLPARABEN, ISOBUTYLPARABEN, 1% PEPTIDE SOLUTION.

Clinical Protocol

Apply both products (active and placebo) twice a day (morning and evening) on perfectly cleaned face (following half-face method, according to the randomization scheme described in the information form given to the subject) around the eyes area, and gently massage until completely absorbed.

Data are submitted to two way "t-test" of student for paired data. The statistic significances are reported as follows: n.s. not significant $p>0.05$; * significant $p<0.05$.

Results on Trans Epidermal Water Loss

Figure 4A:
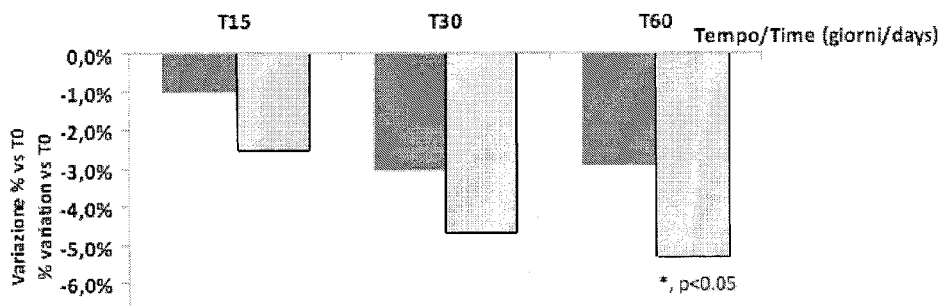
FIGS. 4A-4D.

The graph of FIG. 4A reports the mean of the percentage variations vs T0 obtained for the trans epidermal water loss parameter.

This result demonstrates that DOR agonist peptides can significantly reduce the trans epidermal water loss in human skin. After 60 days, there was 82% reduction of water loss versus placebo.

Results on Skin Moisturization

Figure 4B:
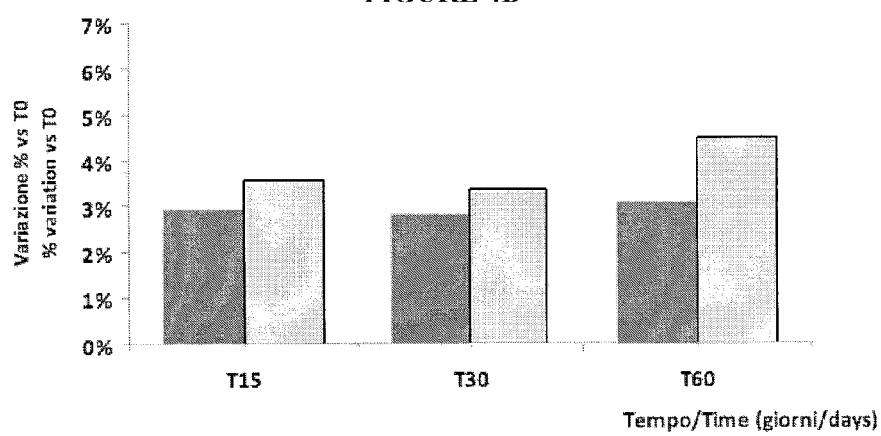

The graph of FIG. 4B reports the mean of the percentage variations vs T0 obtained for the skin moisturizing parameter.

This result demonstrates that DOR agonist peptides can improve the level of natural moisturization of human skin.

Results on Deep Wrinkles

Figure 4C:
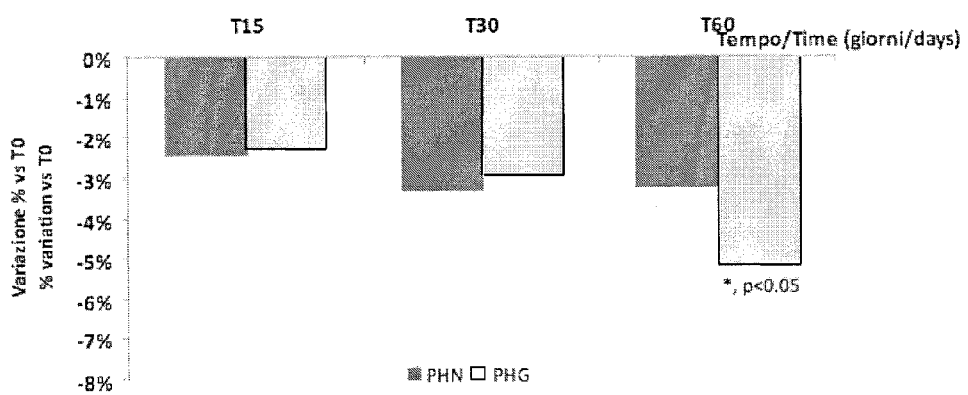

The graph of FIG. 4C reports the mean of the percentage variations vs T0 obtained for the wrinkle depth parameter.

This result demonstrates that DOR agonist peptides can significantly reduce the depth of wrinkles in human skin. In particular, a significant 58% reduction of wrinkles depth versus placebo has been observed.

Results on Skin Wrinkledness

Figure 4D:
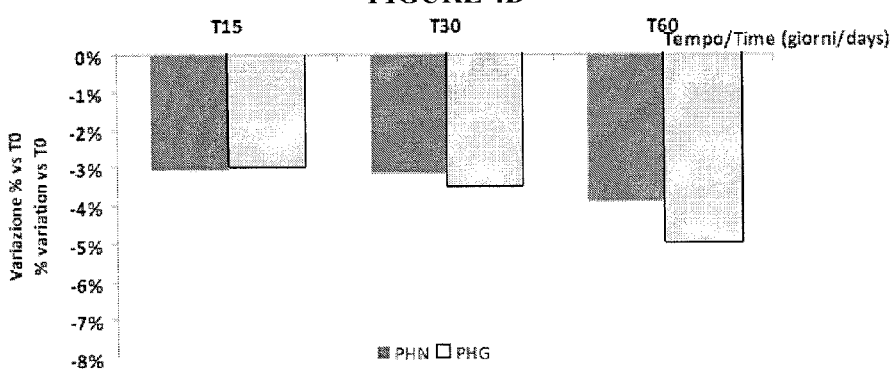

The graph of FIG. 4D reports the mean of the percentage variations vs T0 obtained for the Rz parameter (skin wrinkledness).

This result demonstrates that DOR agonist peptides can improve the smoothness of human skin.

Example 2

Examples of Formulation for Skin Care Including the Peptide YPLDLF (SEQ ID No 1)

Regenerative cream for mature skins
A-Aqueous phase

| | |
|---|---|
| Glycerin | 2.0% |
| Hexylene glycol | 3.0% |
| Xanthane gum | 0.5% |
| Preservatives | qs |
| Carbomer | 0.35% |
| Peptide at 300PMM | 1% |
| Water | qsp. 100% |

B-Oil phase

| | |
|---|---|
| Squalane | 15% |
| Cetyl alcohol | 2% |
| Arachidyl alcohol/behenyl alcohol/arachidylglucoside) | 1% |
| Glycerol stearate | 5% |
| Water | 1.5% |
| NaOH | 0.35% |
| Preservative + fragrance | qs |

Hydrating and emollient lotion
A-Oil phase

| | |
|---|---|
| Ceteareth-2 | 3.5% |
| Ceteareth-21 | 2-4% |
| Wheat germ oil | 3% |
| Cyclomethicone | 7% |
| Octyl Palmitate | 8% |

B-Aqueous phase

| | |
|---|---|
| Water | qsp. 100% |
| Glycerin | 7.0% |
| Hexylene glycol | 3.0% |
| Peptide at 300 PPM | 1% |
| Preservatives | qs |

C-Ingredients added in the emulsion, at a temperature below 40° C.

| | |
|---|---|
| Sodium hyaluronate | 0.1% |
| Water | 5% |
| Tocopherol | 0.05% |
| Vitamin A Palmitate | 0.1% |
| Phospholipides | 0.5% |
| Ceramides 3 | 0.1% |
| Polyacrylamide & $C_{14-13}$ isoparaffine & laureth-7 | 2-3.5% |

Milky solar cream for photo-aged skins
A-Oil phase

| | |
|---|---|
| Glycerol monostearate | 2% |
| PEG-100 stearate | 3% |
| C12-C15 alkyl benzoate | 10% |
| Dimethicone | 5% |
| Tocopherol acetate | 1% |
| Octyl-triazone (Uvinul T150) | 1.5% |
| Butyl Methoxy Dibenzoyl methane (Eusolex 9020) | 2.0% |
| Cetostearylic alcohol | 1% |

B-Aqueous phase

| | |
|---|---|
| Water | qsp. 100% |
| Preservatives | 0.6% |
| Glycerin | 7% |
| Hexylene glycol | 3.0% |
| Carbomer | 0.5% |
| Tetra sodium EDTA | 0.2% |
| Peptide at 300 PPM | 1% |
| HMW sodium hyaluronate | 0.1% |
| Water | 5% |
| NaOH | 0.5% |
| Preservatives + fragrance | qs. |

Anti wrinkles cream post aesthetic surgery
A-Oil phase

| | |
|---|---|
| Squalane | 5% |
| Cetylic alcohol | 2% |
| Dimethicone | 5% |
| Octyl palmitate | 5% |

B-Aqueous phase

| | |
|---|---|
| Butylene glycol | 0.5-4% |
| Water | qsp. 100% |
| Peptide at 300 PPM | 1% |
| Glycerin | 2.0% |
| Hexylene glycol | 3.0% |
| Xanthan gum | 0.5% |
| Preservatives | qs |

C-Ingredients added in the emulsion, at a temperature below 40° C.

| | |
|---|---|
| Tocopherol acetate | 0.1-1% |
| Pyridoxine | 0.01-0.05% |
| Vitamin A palmitate | 0.01-1% |
| D-Panthenol | 0.1-1% |
| Citric acid | 0.1-0.5% |
| Zinc gluconate | 0.1-1% |
| Trisodium citrate | 1-2.5% |
| Water | 5% |

Cleansing lotion for mature skins

| | |
|---|---|
| Polysorbate 20 | 1.0% |
| Caprylyl/capryl glucoside (Oramix CG110) | 2.0% |
| Peptide at 300 PPM | 0.1% |
| PEG-7 glyceryl cocoate | 0.5% |
| Hexylene glycol | 4-5% |
| D-Panthenol | 0.1% |
| Mannitol | 0.02% |
| Preservatives | qs |
| Water | qsp. 100% |

2 in 1 conditioning shampoo for hair repigmentation

| | |
|---|---|
| Water | qs 100% |
| Acrylates crosspolymer-4 | 9% |
| PEG-7 amodimehticone | 1.5% |
| Ammonium lauryl sulfate, ammonium laureth sulfate, lauryl glucoside and cocamide DEA | 13% |
| Peptide at 300 PPM | 1 to 2% |
| NaOH (18% solution) | 0.84% |
| Cocamidopropyl betaine (35% active) | 2% |
| Lauramide DEA | 2% |
| Mica and Titanium dioxide | 0.02% |
| Preservatives | 0.5% |
| Colorant | 0.15% |
| Fragrance | 0.5% |

REFERENCES

Bigliardi et al. 2006, *Differentiation*, 74:174-185.

Bigliardi et al. 2007, *J Invest Dermatol.*, 127(6):1479-88

Bigliardi et al., 2009, *Exp Dermatol.*; 18(5):424-30

Giacomoni et al., 2005, *EMBO reports*, 6, S45-S48.

Kauser et al, 2004, *J Invest Dermatol*, 123:184-195.

Law and Loh, 1993, *Mol. Pharmacol.*, 43: 684-693.

Poumay et al., 2004, Arch Dermatol Res. 296(5):203-11

Vives et al, Biochimic et Biophysica Acta, 2008, 1786, 126-138

Yang et al, 2001, *FEBS Lett.*; 509(2):213-7

Yang et al., 2003, *Peptides*, 24(4):503-8

We claim:

1. A cosmetic method for stimulating pigmentation of skin or pigmenting hair comprising applying a composition to skin or hair in need of said pigmentation wherein said composition comprises a 5 or 6 amino acid peptide selected from the group consisting of rubiscolin-6 and SEQ ID NOs:7-26, wherein said composition contains 0.000005% to 0.002% by weight of said peptide.

2. The method of claim 1, wherein said composition comprises rubiscolin-6.

3. The method of claim 2, comprising applying said composition to the skin of said subject.

4. The method of claim 2, comprising applying said composition to the hair of said subject.

5. The method of claim 2, wherein said composition comprises a peptide having the sequence selected from the group consisting of SEQ ID NOs: 7-26.

6. The method of claim 5, comprising applying said composition to the skin of said subject.

7. The method of claim 5, comprising applying said composition to the hair of said subject.

8. A method for self-tanning skin or pigmenting hair comprising applying a composition to skin or hair in need of said self-tanning or said pigmenting wherein said composition comprises a 5 or 6 amino acid peptide selected from the group consisting of rubiscolin-6 and SEQ ID NOs:7-26, wherein said composition contains 0.000005% to 0.002% by weight of said peptide.

9. The method of claim 8, wherein said composition comprises rubiscolin-6.

10. The method of claim 8, wherein said composition comprises the peptide having the sequence selected from the group consisting of SEQ ID NOs: 7-26.

11. The method of claim 9, comprising applying said composition to the skin of said subject.

12. The method of claim 9, comprising applying said composition to the hair of said subject.

13. The method of claim 10, comprising applying said composition to the skin of said subject.

14. The method of claim 10, comprising applying said composition to the hair of said subject.

15. A cosmetic method for stimulating pigmentation of skin or pigmenting hair comprising applying a composition to skin or hair in need of said pigmentation wherein said composition comprises a 5 or 6 amino acid peptide selected from the group consisting of rubiscolin-6 and SEQ ID NOs:7-26, wherein said composition contains 0.000005% to 0.002% by weight of said peptide and said 5 or 6 amino acid peptide is acetylated, conjugated to a lipid, esterified, glycosylated or amidated.

16. The method of claim 15, wherein said peptide is conjugated to a lipid selected from the group consisting of acetic acid, butyric acid, capronic acid, caprylic acid, caprynic acid, lauric acid, myristic acid, palmitic acid, stearic acid, arachidic acid, behenic acid, lignoceratic acid, palmitolic acid, oleic acid, linoleic acid, γ-linoleic acid, α-linoleic acid, eicosadinoic acid, eicosatrinoic acid, arachidonic acid, eicosapentaenoic acid, docosapentaeoic acid and docosahexaenoic acid.

* * * * *

UNITED STATES PATENT AND TRADEMARK OFFICE
CERTIFICATE OF CORRECTION

PATENT NO. : 9,107,852 B2
APPLICATION NO. : 13/848937
DATED : August 18, 2015
INVENTOR(S) : Auriol et al.

It is certified that error appears in the above-identified patent and that said Letters Patent is hereby corrected as shown below:

In the Specification

Column 14,
Line 20, "OAK inhibitor" should read --(JAK inhibitor--.

Column 15,
Line 26, "OAK inhibitor" should read --(JAK inhibitor--.

Column 19,
Lines 32-40,
"conditions were performed in n=3.
*Oncostatin M (OSM) + Interleukin 17 (IL-17) + Tumor necrosis factor alpha (TNF-α)
At the end of incubation, the supernatants were collected and the RHE were washed in phosphate buffered saline solution (PBS) for in situ immunolabeling.
Immunofluorescent labeling of Acetyl-coenzyme A synthetase, Corneodesmosin, Involucrin, Keratin 10, and Occludin."
should read
--conditions were performed in n=3.
At the end of incubation, the supernatants were collected and the RHE were washed in phosphate buffered saline solution (PBS) for in situ immunolabeling.
*Oncostatin M (OSM) + Interleukin 17 (IL-17) + Tumor necrosis factor alpha (TNF-α)
Immunofluorescent labeling of Acetyl-coenzyme A synthetase, Corneodesmosin, Involucrin, Keratin 10, and Occludin.--.

In the Claims

Column 35,
Line 45, "claim 2" should read --claim 1--.

Signed and Sealed this
Nineteenth Day of April, 2016

Michelle K. Lee
*Director of the United States Patent and Trademark Office*

SEQUENCE LISTING

<160> NUMBER OF SEQ ID NOS: 29

<210> SEQ ID NO 1
<211> LENGTH: 6
<212> TYPE: PRT
<213> ORGANISM: Artificial sequence
<220> FEATURE:
<223> OTHER INFORMATION: Rubiscolin-6

<400> SEQUENCE: 1

Tyr Pro Leu Asp Leu Phe
1               5

<210> SEQ ID NO 2
<211> LENGTH: 7
<212> TYPE: PRT
<213> ORGANISM: artificial
<220> FEATURE:
<223> OTHER INFORMATION: deltorphin
<220> FEATURE:
<221> NAME/KEY: MISC_FEATURE
<222> LOCATION: (2)..(2)
<223> OTHER INFORMATION: D-configuration
<220> FEATURE:
<221> NAME/KEY: MOD_RES
<222> LOCATION: (7)..(7)
<223> OTHER INFORMATION: AMIDATION

<400> SEQUENCE: 2

Tyr Met Phe His Leu Met Asp
1               5

<210> SEQ ID NO 3
<211> LENGTH: 7
<212> TYPE: PRT
<213> ORGANISM: artificial
<220> FEATURE:
<223> OTHER INFORMATION: deltorphin derivative
<220> FEATURE:
<221> NAME/KEY: MISC_FEATURE
<222> LOCATION: (2)..(2)
<223> OTHER INFORMATION: D-configuration
<220> FEATURE:
<221> NAME/KEY: MOD_RES
<222> LOCATION: (7)..(7)
<223> OTHER INFORMATION: AMIDATION

<400> SEQUENCE: 3

Tyr Ala Phe Asp Val Val Gly
1               5

<210> SEQ ID NO 4
<211> LENGTH: 7
<212> TYPE: PRT
<213> ORGANISM: artificial
<220> FEATURE:
<223> OTHER INFORMATION: deltorphin derivative
<220> FEATURE:
<221> NAME/KEY: MISC_FEATURE
<222> LOCATION: (2)..(2)
<223> OTHER INFORMATION: D-configuration
<220> FEATURE:
<221> NAME/KEY: MOD_RES
<222> LOCATION: (7)..(7)
<223> OTHER INFORMATION: AMIDATION

<400> SEQUENCE: 4

Tyr Ala Phe Glu Val Val Gly
1               5

```
<210> SEQ ID NO 5
<211> LENGTH: 17
<212> TYPE: PRT
<213> ORGANISM: artificial
<220> FEATURE:
<223> OTHER INFORMATION: deltorphin derivative
<220> FEATURE:
<221> NAME/KEY: MISC_FEATURE
<222> LOCATION: (2)..(2)
<223> OTHER INFORMATION: D configuration
<220> FEATURE:
<221> NAME/KEY: MOD_RES
<222> LOCATION: (17)..(17)
<223> OTHER INFORMATION: AMIDATION

<400> SEQUENCE: 5

Tyr Leu Phe Ala Asp Val Ala Ser Thr Ile Gly Asp Phe Phe His Ser
1               5                   10                  15

Ile

<210> SEQ ID NO 6
<211> LENGTH: 6
<212> TYPE: PRT
<213> ORGANISM: artificial sequence
<220> FEATURE:
<223> OTHER INFORMATION: Formula (I)
<220> FEATURE:
<221> NAME/KEY: MISC_FEATURE
<222> LOCATION: (3)..(3)
<223> OTHER INFORMATION: X1 = being a non-aromatic hydrophobic amino
      acid, preferably L, I, M, V or A, more preferably L, I, or M
<220> FEATURE:
<221> NAME/KEY: MISC_FEATURE
<222> LOCATION: (5)..(5)
<223> OTHER INFORMATION: X2 = being a non-aromatic hydrophobic amino
      acid, preferably L, I, or M, more preferably L or I
<220> FEATURE:
<221> NAME/KEY: MISC_FEATURE
<222> LOCATION: (6)..(6)
<223> OTHER INFORMATION: X3 = being a hydrophobic amino acid,
      preferably F, L, I, M, V or A, more preferably F, I, or V,

<400> SEQUENCE: 6

Tyr Pro Xaa Asp Xaa Xaa
1               5

<210> SEQ ID NO 7
<211> LENGTH: 6
<212> TYPE: PRT
<213> ORGANISM: artificial
<220> FEATURE:
<223> OTHER INFORMATION: rubiscolin-6 derivative

<400> SEQUENCE: 7

Tyr Pro Ile Asp Leu Phe
1               5

<210> SEQ ID NO 8
<211> LENGTH: 6
<212> TYPE: PRT
<213> ORGANISM: artificial
<220> FEATURE:
<223> OTHER INFORMATION: rubiscolin-6 derivative

<400> SEQUENCE: 8

Tyr Pro Met Asp Leu Phe
1               5

<210> SEQ ID NO 9
<211> LENGTH: 6
```

```
<212> TYPE: PRT
<213> ORGANISM: artificial
<220> FEATURE:
<223> OTHER INFORMATION: rubiscolin-6 derivative

<400> SEQUENCE: 9

Tyr Pro Leu Asp Ile Phe
1               5

<210> SEQ ID NO 10
<211> LENGTH: 6
<212> TYPE: PRT
<213> ORGANISM: artificial
<220> FEATURE:
<223> OTHER INFORMATION: rubiscolin-6 derivative

<400> SEQUENCE: 10

Tyr Pro Leu Asp Leu Leu
1               5

<210> SEQ ID NO 11
<211> LENGTH: 6
<212> TYPE: PRT
<213> ORGANISM: artificial
<220> FEATURE:
<223> OTHER INFORMATION: rubiscolin-6 derivative

<400> SEQUENCE: 11

Tyr Pro Leu Asp Leu Ile
1               5

<210> SEQ ID NO 12
<211> LENGTH: 6
<212> TYPE: PRT
<213> ORGANISM: artificial
<220> FEATURE:
<223> OTHER INFORMATION: rubiscolin-6 derivative

<400> SEQUENCE: 12

Tyr Pro Leu Asp Leu Met
1               5

<210> SEQ ID NO 13
<211> LENGTH: 6
<212> TYPE: PRT
<213> ORGANISM: artificial
<220> FEATURE:
<223> OTHER INFORMATION: rubiscolin-6 derivative

<400> SEQUENCE: 13

Tyr Pro Leu Asp Leu Val
1               5

<210> SEQ ID NO 14
<211> LENGTH: 6
<212> TYPE: PRT
<213> ORGANISM: artificial
<220> FEATURE:
<223> OTHER INFORMATION: rubiscolin-6 derivative

<400> SEQUENCE: 14

Tyr Pro Leu Asp Leu Ala
1               5

<210> SEQ ID NO 15
<211> LENGTH: 6
<212> TYPE: PRT
```

```
<213> ORGANISM: artificial
<220> FEATURE:
<223> OTHER INFORMATION: rubiscolin-6 derivative

<400> SEQUENCE: 15

Tyr Pro Ile Asp Leu Val
1               5

<210> SEQ ID NO 16
<211> LENGTH: 6
<212> TYPE: PRT
<213> ORGANISM: artificial
<220> FEATURE:
<223> OTHER INFORMATION: rubiscolin-6 derivative

<400> SEQUENCE: 16

Tyr Pro Met Asp Leu Val
1               5

<210> SEQ ID NO 17
<211> LENGTH: 6
<212> TYPE: PRT
<213> ORGANISM: artificial
<220> FEATURE:
<223> OTHER INFORMATION: rubiscolin-6 derivative

<400> SEQUENCE: 17

Tyr Pro Leu Asp Ile Val
1               5

<210> SEQ ID NO 18
<211> LENGTH: 6
<212> TYPE: PRT
<213> ORGANISM: artificial
<220> FEATURE:
<223> OTHER INFORMATION: rubiscolin-6 derivative

<400> SEQUENCE: 18

Tyr Pro Ile Asp Ile Val
1               5

<210> SEQ ID NO 19
<211> LENGTH: 6
<212> TYPE: PRT
<213> ORGANISM: artificial
<220> FEATURE:
<223> OTHER INFORMATION: rubiscolin-6 derivative

<400> SEQUENCE: 19

Tyr Pro Met Asp Ile Val
1               5

<210> SEQ ID NO 20
<211> LENGTH: 6
<212> TYPE: PRT
<213> ORGANISM: artificial
<220> FEATURE:
<223> OTHER INFORMATION: rubiscolin-6 derivative

<400> SEQUENCE: 20

Tyr Pro Ile Asp Leu Val
1               5

<210> SEQ ID NO 21
<211> LENGTH: 6
<212> TYPE: PRT
<213> ORGANISM: artificial
```

```
<220> FEATURE:
<223> OTHER INFORMATION: rubiscolin-6 derivative

<400> SEQUENCE: 21

Tyr Pro Ile Asp Met Val
1               5

<210> SEQ ID NO 22
<211> LENGTH: 6
<212> TYPE: PRT
<213> ORGANISM: artificial
<220> FEATURE:
<223> OTHER INFORMATION: rubiscolin-6 derivative

<400> SEQUENCE: 22

Tyr Pro Ile Asp Ile Ile
1               5

<210> SEQ ID NO 23
<211> LENGTH: 6
<212> TYPE: PRT
<213> ORGANISM: artificial
<220> FEATURE:
<223> OTHER INFORMATION: rubiscolin-6 derivative

<400> SEQUENCE: 23

Tyr Pro Met Asp Ile Ile
1               5

<210> SEQ ID NO 24
<211> LENGTH: 5
<212> TYPE: PRT
<213> ORGANISM: artificial
<220> FEATURE:
<223> OTHER INFORMATION: rubiscolin-6 derivative

<400> SEQUENCE: 24

Tyr Pro Met Asp Leu
1               5

<210> SEQ ID NO 25
<211> LENGTH: 5
<212> TYPE: PRT
<213> ORGANISM: artificial
<220> FEATURE:
<223> OTHER INFORMATION: rubiscolin-6 derivative

<400> SEQUENCE: 25

Tyr Pro Ile Asp Leu
1               5

<210> SEQ ID NO 26
<211> LENGTH: 5
<212> TYPE: PRT
<213> ORGANISM: artificial
<220> FEATURE:
<223> OTHER INFORMATION: rubiscolin-6 derivative

<400> SEQUENCE: 26

Tyr Pro Met Asp Ile
1               5

<210> SEQ ID NO 27
<211> LENGTH: 5
<212> TYPE: PRT
<213> ORGANISM: artificial
<220> FEATURE:
```

```
<223> OTHER INFORMATION: DPDPE

<400> SEQUENCE: 27

Asp Pro Asp Pro Glu
1               5

<210> SEQ ID NO 28
<211> LENGTH: 5
<212> TYPE: PRT
<213> ORGANISM: artificial
<220> FEATURE:
<223> OTHER INFORMATION: Rubiscolin-5

<400> SEQUENCE: 28

Tyr Pro Leu Asp Leu
1               5

<210> SEQ ID NO 29
<211> LENGTH: 4
<212> TYPE: PRT
<213> ORGANISM: artificial
<220> FEATURE:
<223> OTHER INFORMATION: Rubiscolin-4

<400> SEQUENCE: 29

Tyr Pro Leu Asp
1
```